US008609418B2

(12) United States Patent
Mao et al.

(10) Patent No.: US 8,609,418 B2
(45) Date of Patent: Dec. 17, 2013

(54) GENETIC TRANSFORMATION OF JATROPHA CURCAS

(75) Inventors: Hui Zhu Mao, Singapore (SG); Jian Ye, Singapore (SG); Nam Hai Chua, New York, NY (US)

(73) Assignee: Joil (S) Pte Ltd., Singapore (SG)

( * ) Notice: Subject to any disclaimer, the term of this patent is extended or adjusted under 35 U.S.C. 154(b) by 105 days.

(21) Appl. No.: 13/139,592

(22) PCT Filed: Dec. 15, 2009

(86) PCT No.: PCT/SG2009/000479
§ 371 (c)(1),
(2), (4) Date: Jun. 14, 2011

(87) PCT Pub. No.: WO2010/071608
PCT Pub. Date: Jun. 24, 2010

(65) Prior Publication Data
US 2011/0247099 A1    Oct. 6, 2011

Related U.S. Application Data

(60) Provisional application No. 61/122,454, filed on Dec. 15, 2008.

(51) Int. Cl.
*C12N 5/00* (2006.01)
*A01H 5/00* (2006.01)
(52) U.S. Cl.
USPC .......................... 435/430; 800/298; 800/306
(58) Field of Classification Search
USPC ........... 435/430, 410, 420; 800/298, 306, 295
See application file for complete search history.

(56) References Cited

U.S. PATENT DOCUMENTS

| 7,005,298 B1* | 2/2006 | Saxena et al. ................. 435/420 |
| 2006/0260012 A1* | 11/2006 | Khan ........................... 800/287 |
| 2008/0196121 A1 | 8/2008 | Murali et al. |

FOREIGN PATENT DOCUMENTS

| CN | 1799340 A | 7/2006 |
| EP | 1817956 A2 | 8/2007 |
| KR | 10-0856930 B1 | 9/2008 |
| KR | 100856930 B1 | 9/2008 |
| WO | 03/002751 A2 | 1/2003 |
| WO | 2008/068498 A2 | 6/2008 |

OTHER PUBLICATIONS

Li et al. Establishment of an *Agrobacterium*-mediated cotyledon disc transformation method for *Jatropha curcas*. Plant Cell Tiss Organ Cult (Feb. 2008) 92:173-181.*
Shrivastava et al. In vitro clonal propagation of physic nut (*Jatropha curcas* L.): Influence of additives. IJIB 2008, vol. 3, No. 1, pp. 73-79.*
Vengadesan et al. In vitro propagation of *Acacia* species—a review. Plant Science, vol. 163, No. 4, Oct. 2002, pp. 663-671.*
English translation of Yuan et al. Research progress of tissue culture and rapid propagation of *Jatropha curcas*. Journal of Anhui Agriculture, vol. 36, Issue No. 29, Oct. 2008, 22 pp.*
Yuan et al. Research progress of tissue culture and rapid propagation of *Jatropha curcas*. Journal of Anhui Agri. Sci. vol. 29, No. 36, Oct. 2008, 12587-12588, 12610.*
Sardana, J. et al., "An Expeditious Method for Regeneration of Somatic Embryos in *Jatropha curcas* L.," Phytomorphology, vol. 50, Nos. 3-4, pp. 239-242, Jan. 1, 2000, XP009144284.
Deore, A.C. et al., "High-Frequency Plant Regeneration from Leaf-Disc Cultures of *Jatropha curcas* L.: An Important Biodiesel Plant," Plant Biotechnology Reports, vol. 2, No. 1, Apr. 2008, pp. 7-11, XP002674111.
PhytoTechnology Laboratories, Inc., "Tissue Culture Media-Composition," Product Information Sheet, 2003, XP002674112, 7 pages.
Extended European Search Report—EP Communication dated May 29, 2012, Reference: GMW/P42736EP, Application No./Patent No. 09833762.0-2403 / 2373152 PCT/SG2009000479, Applicant: Temasek Life Sciences Laboratory Limited, 10 pages.
Yuan, Rui-Ling et al., "Research Progress of Tissue Culture and Rapid Propagation of *Jatropha curcas*," Journal of Anhui Agri. Sci., vol. 29, No. 36, Oct. 2008, abstract only in English, 4 pages.
Chinese Office Action and Search Report, Application No. 200980150544.3 dated Dec. 15, 2009, Applicant: Temasek Life Sciences Laboratory Limited, 11 pages.
Sujatha, M. et al., "Role of biotechnological interventions in the improvement of castor (*Ricinus communis* L.) and *Jatropha curcas* L.," Biotechnology Advances, Oct. 2008, vol. 26(5), pp. 424-435.
Rajore, S. & Batra, A., "An alternative source for regenerable organogenic callus induction in *Jatropha curcas* L," Indian Journal of Biotechnology, Oct. 2007, vol. 6(4), pp. 545-548.
Li, M. et al., "Established of an *Agrobacterium*-mediated cotyledon disc transformation method for *Jatropha curcas*," Plant Cell, Tissue and Organ Culture 2008, vol. 92, pp. 173-181.
He, Y. et al., "*Agrobacterium tumefaciens*-mediated Transformation of *Jatropha curcas*: Factors Affecting Transient Transformation Efficiency and Morphology Analysis of Transgenic Calli," Silvae Genetica, Dec. 3, 2009, vol. 58 (3), pp. 123-128.
Cernac, A. et al., "Wrinkled1 encodes an AP2/EREB domain protein involved in the control of storage compound biosynthesis in *Arabidopsis*," The Plant Journal, Blackwell Scientific Publications, Oxford, GB, vol. 40, No. 4, Nov. 1, 2004, pp. 575-585, XP002420086.
Extended European Search Report, Application No./Patent No. 12173513.8-2403, dated Sep. 17, 2012, Applicant: Temasek Life Sciences Laboratory, 10 pages.
Li, M. et al., "The Study of Factors Influencing *Agrobacterium*-Mediated *Jatropha* Gene Transformation," Journal of Molecular Cell Biology, vol. 30, No. 1, Feb. 15, 2006, Abstract included, pp. 83-89 (plus two additional pages), 9 pages.
Chinese Office Action, Search Report, Mailed: May 29, 2013, CN Application No. 201210138483.2; Application date: Dec. 15, 2009, Temasek Life Sciences Laboratory Limited, 11 pages.

* cited by examiner

*Primary Examiner* — June Hwu
(74) *Attorney, Agent, or Firm* — Rothwell, Figg, Ernst & Manbeck P.C.

(57) ABSTRACT

The present invention relates to methods for the regeneration and *Agrobacterium*-mediated transformation of plants in the genera of *Jatropha*, more specifically, in *Jatropha curcas*.

16 Claims, 5 Drawing Sheets

GENETIC TRANSFORMATION OF JATROPHA CURCAS

CROSS-REFERENCE TO RELATED APPLICATION

The present application is a national stage filing under 35 U.S.C. §371 of PCT/SG2009/000479, filed on 15 Dec. 2009, and claims the benefit of priority to U.S. provisional patent application Ser. No. 61/122,454 filed 15 Dec. 2008, each application is incorporated herein by reference in its entirety.

BACKGROUND OF THE INVENTION

The present invention relates to the field of plant regeneration and transformation, particularly to methods for the regeneration and transformation of *Jatropha*. More specifically, the present invention relates to a method and media compositions for regeneration and transformation of plants of *Jatropha curcas*.

The publications and other materials used herein to illuminate the background of the invention or provide additional details respecting the practice, are incorporated by reference, and for convenience are respectively grouped in the Bibliography.

The world is facing dwindling supply is fossil fuel and worsening Green House Effect. There is an urgent demand to increase production and consumption of renewable energy. Biofuels have been recognized as a national priority for many countries in their search for alternative sources to meet their energy security needs and at the same time help reduce $CO_2$ emissions that cause the Green House Effect. The demand for biofuel has put increasing pressure on food production. For example, to satisfy the biofuel need for Germany in 2017 as mandated by the German government the entire farm land of this country would have to be used for growing bioenergy crops with no land left for food production. To ease this competition for land and to satisfy our need for renewable fuels, there is a strong need to utilize marginal land for bioenergy production.

*Jatropha curcas* is a small woody plant belonging to the Euphorbiaceae family. Several unique characters of *Jatropha curcas* make it an ideal plant for biodiesel production. These include its rapid growth, easy propagation, low cost of seeds, high oil content, short gestation period, wide adaptability, drought tolerance and the ability to thrive on degraded soils. Moreover, its plant size renders convenient collection of seed (Jones, 1991; Sujatha et al., 2008).

However, *Jatropha* suffers from several shortcomings that may limit its wide adoption. The productivity of the plant is constrained by the unfavourable male to female flower ratio and its oil content has not been optimized by breeding. This plant is also sensitive to biotic stresses such as viral (Narayanna et al., 2007), fungal and bacterium pathogens and abiotic stresses, especially cold and drought (http colon www dot jatropha dot org). The presence of several toxic components (e.g. the protein toxin, curcin, and the cancer-causing agent phorbol esters) in seeds and leaves of the plant possess health hazards for farmers and bioprocess workers in the *Jatropha* industry.

The traditional way to improve on quality traits of plants is by breeding for superior genotypes. However, an assessment of genetic diversity using molecular markers disclosed low inter-accessional variability amongst local *J. curcas* germplasm (Sujatha at al., 2008). Therefore, alternative genetic manipulation tools, such as genetic transformation methods, are urgently required to provide additional strategies for genetic improvement of this crop. *Agrobacterium*-mediated genetic transformation has become the principal choice for generating transgenic plants. However, very few reports have appeared on the use of *Agrobacterium*-mediated transformation of plants belonging to the Euphorbiaceae family. The only one reported transformation protocol for *Jatropha* (Li et al., 2008) is not reproducible in our hands.

Thus, there is a need for methods of transforming *J. curcas* to provide means for genetic improvement in this crop species.

SUMMARY OF THE INVENTION

The present invention relates to methods for the regeneration and *Agrobacterium*-mediated transformation of plants in the genera of *Jatropha*, more specifically, in *Jatropha curcas*.

Thus, in one aspect the present invention provides an efficient and reproducible plant regeneration protocol for *J. curcas* by optimizing tissue culture and shoot regeneration conditions. This regeneration protocol has been used in combination with *Agrobacterium*-mediated transformation to produce $T_0$ transgenic *Jatropha* shoots/plants. The present invention also provides the use of a grafting step using $T_0$ transgenic shoots as scions and non-transgenic plants as root stocks. This grafting step obviates the need for regenerated plants to produce roots in tissue culture and considerably shortens the time for transgenic shoots to flower and produce $T_1$ seeds.

In one embodiment, the present invention provides a method of regenerating *J. curcas* plants. According to this embodiment, explants are obtained from cotyledons from 5-7 day old seedlings. The explants are cultured on callus formation medium which comprises MS mineral salts, B5 vitamins, citric acid, glutamine, casein hydrolysate, sucrose and 6-benzylaminopurine (6-BA) and 1-naphthaleneacetic acid (NAA) as plant hormones. Callus tissue is then transferred to a first shoot regeneration medium which comprises MS mineral salts, B5 vitamins, citric acid, glutamine, casein hydrolysate, adenine, sucrose and 6-BA and 3-indolebutyric acid (IBA) as plant hormones. Any shoots that regenerated from the callus tissue are transferred to a second shoot regeneration medium which comprises MS mineral salts, B5 vitamins, citric acid, glutamine, casein hydrolysate, sucrose and 6-BA, IBA and gibberellic acid ($GA_3$) as plant hormones. Callus tissue with no regenerates shoots are transferred to a third shoot regeneration medium which comprises MS mineral salts, B5 vitamins, citric acid, glutamine, casein hydrolysate, sucrose and 6-BA and IBA as plant hormones for further regeneration of shoots. The shoots that have regenerated are transferred to a shoot elongation medium which comprises MS mineral salts, B5 vitamins, citric acid, glutamine, casein hydrolysate, sucrose and 6-BA and $GA_3$ as plant hormones for elongation and bud multiplication. Elongated shoots are transferred to a rooting medium which comprises MS mineral salts, B5 vitamins, sucrose and IBA. After rooting, the plantlets are transferred to soil. Alternatively, the elongated shoots can be grafted to *J. curcas* root stock.

In a second embodiment, the present invention provides a method for *Agrobacterium*-mediated transformation of *J. curcas* plants. According to this embodiment, the *Agrobacterium*-mediated transformation of *J. curcas* utilizes the same basic scheme as described above for the regeneration of *J. curcas*. For transformation, the explants are first co-cultured with *Agrobacterium* cells prior to transfer to the callus formation medium with subsequent transfers to the shoot regeneration media, shoot elongation medium and rooting medium as described above. The co-culturing medium comprises MS mineral salts, B5 vitamins, citric acid, glutamine, casein hydrolysate, sucrose, glucose, acetosyringone and 6-BA and NAA as plant hormones. The callus formation medium is the same as for regeneration except that it further comprises a selective agent and an *Agrobacterium* eradicant. Similarly, the shoot regeneration media further comprise a selective agent and an *Agrobacterium* eradicant. For transformation, culturing on the callus formation medium is performed in the dark. Conventional selective agents can be used for the *Agrobacterium*-mediated transformation of *J. curcas* plants. Examples of selective agents include, but are not limited to, the herbicide BASTA, hygromycin and the like.

BRIEF DESCRIPTION OF THE FIGURES

FIG. 3A: *J. curcas* MD 5 day's seedling suitable for transformation. FIG. 3B: Callus formation and shoot generation. Left, cotyledons inoculated with *Agrobacterium* without carrying any vector. Right, cotyledons inoculated with *Agrobacterium* carrying a vector with a trait gene. Note shoot regeneration from explants. FIG. 3C: an enlarged view of hygromycin-resistant callus and shoot-like organs on the surface of brownish cotyledons. FIG. 3D: Regeneration of hygromycin-resistant shoots of *J. curcas*. FIG. 3E: Shoot elongation. FIG. 3F: Rooting of transgenic shoots. FIG. 3G: High rooting efficacy for transgenic *J. curcas*. FIG. 3H: Transgenic *J. curcas* grown on soil. FIG. 3I and FIG. 3J: Transgenic *J. curcas* shoots grafted onto non-transgenic rootstock. White arrow indicates the grafting site. FIG. 3K: Transgenic *J. curcas* flowering and seeding. The scale bars indicate 10 mm.

FIGS. 5A-5P show the expression of GFP in $T_0$ plant root (FIG. 5B, FIG. 5D), male flower (FIG. 5F, FIG. 5H), and $T_1$ seeds 3 week after fertilization (FIG. 5J, FIG. 5 K, FIG. 5L, FIG. 5N, FIG. 5O, FIG. 5P). FIG. 5A, FIG. 5C, FIG. 5E, FIG. 5G, FIG. 5I and FIG. 5M are wildtype controls for every plant organ. The scale bars indicate 2 mm.

DETAILED DESCRIPTION OF THE INVENTION

Figure 1:
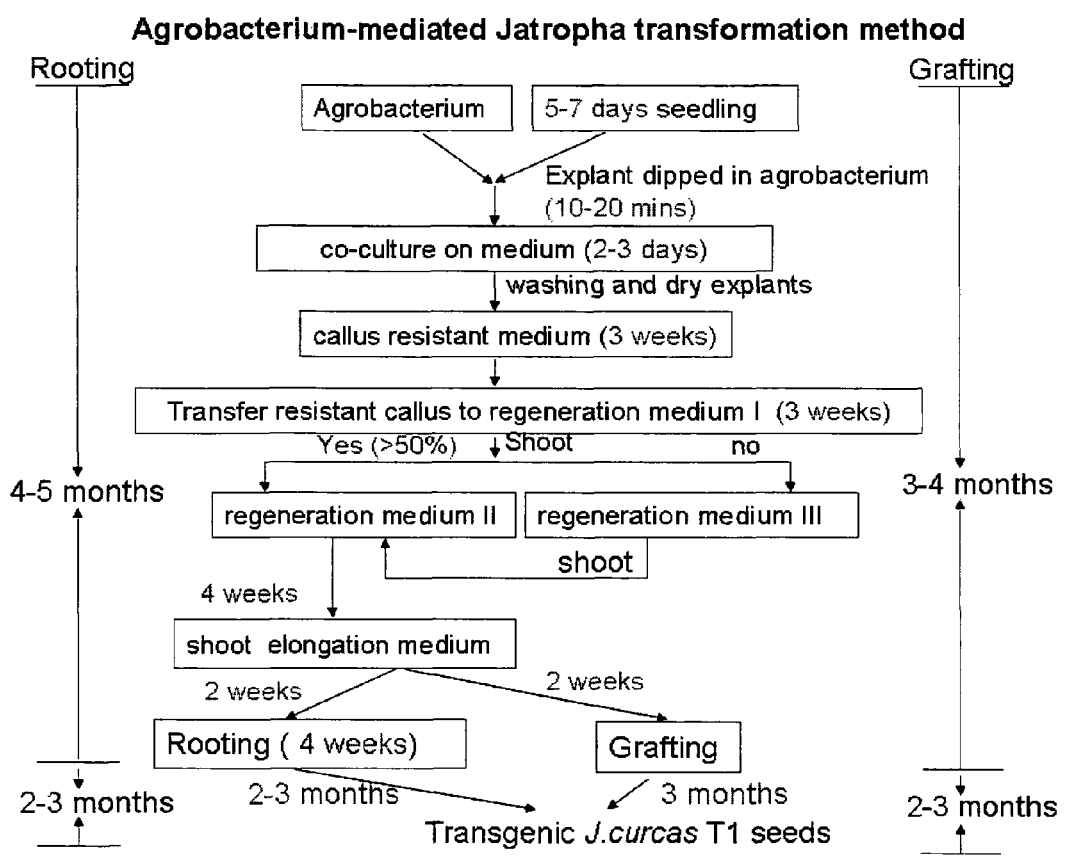
FIG. 1 illustrates an *Agrobacterium*-mediated *Jatrohpa* transformation method in accordance with the present invention. The time scale listed in the left is to use rooting protocol while the left is to use grafting protocol.

The present invention relates to methods for the regeneration and *Agrobacterium*-mediated transformation of plants in the genera of *Jatropha*, more specifically, in *Jatropha curcas*.

In one aspect, the present invention provides a method of regenerating *J. curcas* plants. According to this embodiment, explants are obtained from cotyledons from about 5 day to about 12 day old seedlings, preferably about 5-7 day old seedlings. The culturing is performed in the light at 25° C.±2° C. in a 16 h light (100 μmol/m²S)/8 h dark cycle. The seedlings are grown in tissue culture. Seed kernels of *J. curcas* are surface sterilized using conventional techniques and immersed in sterile water overnight at 28° C. in the dark. The endosperm-free embryos are germinated on hormone free germination medium with the radicals in contact with the medium. The germination medium comprises ½ strength MS mineral salts, B5 vitamins and sucrose. The concentration of sucrose is about 5% (w/v). The germination medium may further comprise a buffer. In one embodiment, the buffer is 2-(4-morpholino)ethanesulfonic acid (MES) at about 0.5 g/L at a pH of about 5.6. The germination medium is solidified with agar or phytogel. The culturing is performed in the light at 25° C.±1° C. in a 16 h light (100 μmol/m²S)/8 h dark cycle.

The explants are cultured on callus formation medium in the dark for about 2 weeks to about 3 weeks, preferably about three weeks. The callus formation medium comprises MS mineral salts, B5 vitamins, citric acid, glutamine, casein hydrolysate, sucrose and 6-benzylaminopurine (6-BA) and 1-naphthaleneacetic acid (NAA) as plant hormones. The concentration of citric acid is about 10 mg/L to about 30 mg/L, preferably about 10 mg/L. The concentration of glutamine is about 150 mg/L to about 200 mg/L, preferably about 150 mg/L. The concentration of casein hydrolysate is about 100 mg/L. The concentration of sucrose is about 3%. The concentration of 6-BA is about 1.5 mg/L. The concentration of NAA is about 0.05 mg/L. The callus formation medium preferably further comprises $MgCl_2$ at a concentration of about 0.5 g/L to about 0.95 g/L, preferably 0.5 g/L. The callus formation medium has a pH of about 5.8 to about 6.0. The callus formation medium is solidified with agar or phytagel, preferably phytagel at a concentration of about 2.5 g/L to about 3 g/L, preferably 2.5 g/L.

Callus tissue is then transferred to a first shoot regeneration medium and cultured in the light for about 2 weeks to about 3 weeks, preferably about three weeks. The first shoot regeneration medium comprises MS mineral salts, B5 vitamins, citric acid, glutamine, casein hydrolysate, adenine, sucrose and 6-BA and 3-indolebutyric acid (IBA) as plant hormones. The concentrations of the citric acid, glutamine, casein hydrolysate and 6-BA are the same as in the callus formation medium. The concentration of adenine is about 2 mg/L to about 4 mg/L, preferably about 2 mg/L. The concentration of IBA is about 0.05 mg/L. The first shoot regeneration medium preferably further comprises $MgCl_2$ at a concentration of about 0.5 g/L to about 0.95 g/L, preferably 0.5 g/L. The first shoot regeneration medium has a pH of about 5.8 to about 6.0. The first shoot regeneration medium is solidified with agar or phytagel, preferably phytagel at a concentration of about 2.5 g/L to about 3.0 g/L, preferably 2.5 g/L.

Any shoots that regenerated from the callus tissue are transferred to a second shoot regeneration medium and cultured in the light for about 3 weeks to about 4 weeks, preferably about four weeks. The second shoot regeneration medium comprises MS mineral salts, B5 vitamins, citric acid, glutamine, casein hydrolysate, sucrose and 6-BA, IBA and gibberellic acid ($GA_3$) as plant hormones. The concentrations of the citric acid, glutamine, casein hydrolysate, 6-BA and IBA are the same as in the first shoot regeneration medium. The concentration of $GA_3$ is about 0.05 mg/L to about 0.5 mg/L, preferably about 0.5 mg/L. The second shoot regeneration medium preferably further comprises $MgCl_2$ at a concentration of about 0.5 g/L. The second shoot regeneration medium has a pH of about 5.8 to about 6.0. The second shoot regeneration medium is solidified with agar or phytagel, preferably agar at a concentration of about 6.5 g/L to about 7 g/L, preferably 7 g/L.

Callus tissue with no regenerates shoots are transferred to a third shoot regeneration medium and cultured in the light for about 4 weeks to about 5 weeks, preferably about 4 weeks. The third shoot regeneration medium comprises MS mineral salts, B5 vitamins, citric acid, glutamine, casein hydrolysate, sucrose and 6-BA and IBA as plant hormones for further regeneration of shoots. The concentration of the citric acid, glutamine, casein hydrolysate, 6-BA and IBA are the same as in the first shoot regeneration medium. The third shoot regeneration medium preferably further comprises $MgCl_2$ at a concentration of about 0.5 g/L to about 0.95 g/L, preferably 0.5 g/L. The third shoot regeneration medium has a pH of about 5.8 to about 6.0. The third shoot regeneration medium is solidified with agar or phytagel, preferably phytagel at a concentration of about 2.5 g/L to about 3 g/L, preferably 2.5 g/L.

The shoots that have regenerated on the second shoot regeneration medium are transferred to a shoot elongation medium and cultured in the light for about 2 weeks to about 3 weeks, preferably about two weeks. The shoot elongation medium comprises MS mineral salts, B5 vitamins, citric acid, glutamine, casein hydrolysate, sucrose and 6-BA and $GA_3$ as plant hormones for elongation and bud multiplication. The concentrations of the citric acid, glutamine and casein hydrolysate are the same as in the first shoot regeneration medium. The concentration of 6-BA is about 0.3 mg/L. The concentration of $GA_3$ is about 0.1 mg/L to about 0.5 mg/L, preferably about 0.1 mg/L. The shoot elongation medium has a pH of about 5.8 to about 6.0. The shoot elongation medium is solidified with agar or phytagel, preferably agar at a concentration of about 6.5 g/L to about 7 g/L, preferably 7 g/L.

Elongated shoots are transferred to a rooting medium and cultured in the light for about 3 weeks to about 4 weeks, preferably about four weeks. The rooting medium comprises MS mineral salts, B5 vitamins, sucrose and IBA. The concentration of sucrose is about 3%. The concentration of IBA is about 0.07 mg/L. The rooting medium has a pH of about 5.6. The rooting medium is solidified with agar or phytagel, preferably phytagel at a concentration of about 2.2 g/L. After rooting, the plantlets are transferred to soil. Alternatively, the elongated shoots can be grafted to *J. curcas* root stock using conventional techniques instead of being transferred to the rooting medium.

In a second aspect, the present invention provides a method for *Agrobacterium*-mediated transformation of *J. curcas* plants. According to this embodiment, the *Agrobacterium*-mediated transformation of *J. curcas* utilizes the same basic scheme as described above for the regeneration of *J. curcas*. Vectors containing DNA of interest are introduced into *Agrobacterium* using conventional techniques, such as electroporation. Transformed *Agrobacterium* cells are cultured prior to use using conventional techniques. In accordance with one such technique, *Agrobacterium* cells are inoculated into LB medium supplemented with kanamycin and carbicillin. The concentration of kanamycin is about 25 mg/L to about 100 mg/L, preferably about 50 mg/L. The concentration of carbicillin is about 50 mg/L to about 100 mg/L, preferably about 100 mg/L. The *Agrobacterium* cells are grown overnight at 28° C., 250 rpm. The *Agrobacterium* cells are collected by centrifugation and re-suspended in liquid MS medium supplemented with sucrose, glucose, acetosyringone (AS), 6-BA and NAA. The concentration of sucrose is about 30 g/L.

The concentration of glucose is about 10 g/L. The concentration of AS is about 20 mg/L. The concentration of 6-BA is about 1.5 mg/L. The concentration of NAA is about 0.05 mg/L to about 0.1 mg/L, preferably about 0.1 mg/L.

For transformation, the explants are first co-cultured with *Agrobacterium* cells prior to transfer to the callus formation medium with subsequent transfers to the shoot regeneration media, shoot elongation medium and rooting medium as described above. The co-culturing is performed in the dark for about 2-3 days. The co-culturing medium comprises MS mineral salts, B5 vitamins, citric acid, glutamine, casein hydrolysate, sucrose, AS and 6-BA and NAA as plant hormones. The concentrations of citric acid, glutamine, casein hydrolysate and sucrose are the same as in the callus formation medium. The concentration of AS is about 20 mg/L. The concentration of 6-BA is about 1.5 mg/L. The concentration of NAA is about 0.05 mg/L to about 0.1 mg/L, preferably about 0.05 mg/L. The co-culturing medium may further comprise a suitable buffer. In one embodiment, the buffer is MES. The concentration of MES is about 0.5 g/L at a pH of about 5.0 to about 5.2.

The callus formation medium used for the *Agrobacterium*-mediated transformation of *J. curcas* is the same as that used for regeneration except that it further comprises a selective agent and an *Agrobacterium* eradicant. The selective agent may be any selective agent for which a marker gene, such as described below, has been included in the transformed *Agrobacterium*. In one embodiment, the selective agent is hygromycin at a concentration of about 3 mg/L to about 5 mg/L, preferably 3.5 mg/L. In another embodiment, the selective agent is glufosinate ammonium at a concentration of about 1 mg/L. The *Agrobacterium* eradicant may be any conventional eradicant, such as cefotaxinme, and the like. In one embodiment, the *Agrobacterium* eradicant is cefotaxinme at a concentration of about 100 mg/L to about 150 mg/L, preferably 100 mg/L. Culturing on the callus formation medium for *Agrobacterium*-mediated transformation is performed in the dark for about 2 weeks to about 3 weeks, preferably about 3 weeks.

The callus tissue is then treated as described above with respect to the regeneration of *J. curcas* with transfers and culturing in the light as described above to the first shoot regeneration medium, second shoot regeneration medium, third shoot regeneration medium, shoot elongation medium, rooting medium or grafting. The first shoot regeneration medium used for the *Agrobacterium*-mediated transformation of *J. curcas* is the same as that used for regeneration except that it further comprises a selective agent and an *Agrobacterium* eradicant. The selective agent may be any selective agent for which a marker gene, such as described below, has been included in the transformed *Agrobacterium*. In one embodiment, the selective agent is hygromycin at a concentration of about 3 mg/L to about 5 mg/L, preferably 3.5 mg/L. In another embodiment, the selective agent is glufosinate ammonium at a concentration of about 1 mg/L. The *Agrobacterium* eradicant may be any conventional eradicant, such as cefotaxinme. In one embodiment, the *Agrobacterium* eradicant is cefotaxinme at a concentration of about 100 mg/L to about 150 mg/L, preferably 100 mg/L.

The second shoot regeneration medium used for the *Agrobacterium*-mediated transformation of *J. curcas* is the same as that used for regeneration except that it further comprises a selective agent and an *Agrobacterium* eradicant. The selective agent may be any selective agent for which a marker gene, such as described below, has been included in the transformed *Agrobacterium*. In one embodiment, the selective agent is hygromycin at a concentration of about 4 mg/L to about 5 mg/L, preferably 4 mg/L. In another embodiment, the selective agent is glufosinate ammonium at a concentration of about 1 mg/L. The *Agrobacterium* eradicant may be any conventional eradicant, such as cefotaxinme. In one embodiment, the *Agrobacterium* eradicant is cefotaxinme at a concentration of about 100 mg/L to about 150 mg/L, preferably 100 mg/L.

The third shoot regeneration medium used for the *Agrobacterium*-mediated transformation of *J. curcas* is the same as that used for regeneration except that it further comprises a selective agent and an *Agrobacterium* eradicant. The selective agent may be any selective agent for which a marker gene, such as described below, has been included in the transformed *Agrobacterium*. In one embodiment, the selective agent is hygromycin at a concentration of about 3 mg/L to about 5 mg/L, preferably 3.5 mg/L. In another embodiment, the selective agent is glufosinate ammonium at a concentration of about 1 mg/L. The *Agrobacterium* eradicant may be any conventional eradicant, such as cefotaxinme. In one embodiment, the *Agrobacterium* eradicant is cefotaxinme at a concentration of about 100 mg/L to about 150 mg/L, preferably 100 mg/L.

The shoot elongation medium and the rooting medium used for the *Agrobacterium*-mediated transformation of *J. curcas* are the same as that used for regeneration.

The DNA that is inserted (the DNA of interest) into plants of the genera *Jatropha* is not critical to the transformation process. Generally the DNA that is introduced into a plant is part of a construct. The DNA may be a gene of interest, e.g., a coding sequence for a protein, or it may be a sequence that is capable of regulating expression of a gene, such as an antisense sequence, a sense suppression sequence or a miRNA sequence. The construct typically includes regulatory regions operatively linked to the 5' side of the DNA of interest and/or to the 3' side of the DNA of interest. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670 and 2006/0248616. The expression cassette may additionally contain selectable marker genes. See, U.S. Pat. No. 7,205,453 and U.S. Patent Application Publication Nos. 2006/0218670 and 2006/0248616.

Generally, the expression cassette will comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, WO 02/36782, U.S. Pat. No. 7,205,453 and U.S. Patent Application Publication Nos. 2006/0248616 and 2007/0143880, and those references cited therein. This list of selectable marker genes is not meant to be limiting. Any selectable marker gene can be used.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV$^{35S}$ promoter (Odell et al., 1985); rice actin (McElroy et al., 1990); ubiquitin (Christensen and Quail, 1989 and Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are expressed locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters are described in U.S. Pat. Nos. 6,506,962, 6,575,814, 6,972,349 and 7,301,069 and in U.S. Patent Application Publication Nos. 2007/0061917 and 2007/0143880.

Where appropriate, the DNA of interest may be optimized for increased expression in the transformed plant. That is, the coding sequences can be synthesized using plant-preferred codons for improved expression. Methods are available in the art for synthesizing plant-preferred genes. See, for example, U.S. Pat. Nos. 5,380,831, 5,436,391, and 7,205,453 and U.S. Patent Application Publication Nos. 2006/0218670 and 2006/0248616.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast*

Genetics and Molecular Biology (Academic Press, New York, 1991); Harlow and Lane, 1988, Antibodies, (Cold Spring Harbor Laboratory Press, Cold Spring Harbor, N.Y.); Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Fire et al., RNA Interference Technology: From Basic Science to Drug Development, Cambridge University Press, Cambridge, 2005; Schepers, RNA Interference in Practice, Wiley—VCH, 2005; Engelke, RNA Interference (RNAi): The Nuts & Bolts of siRNA Technology, DNA Press, 2003; Gott, RNA Interference, Editing, and Modification: Methods and Protocols (Methods in Molecular Biology), Human Press, Totowa, N.J., 2004; Sohail, Gene Silencing by RNA Interference: Technology and Application, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Materials and Methods

Plant Materials and Culture Methods:
Jatropha curcas (L.) MD seeds were obtained from Indonesia. After removing the outer seed coat, seeds kernel were surface sterilized for 60 seconds with 75% (v/v) ethanol, following immersed in 10% (v/v) $H_2O_2$ for 1 h, then rinsed with sterile water for two times, finally immersed in sterile water overnight at 28° C. in darkness. The endosperm-free embryos were germinated on hormone-free half-strength Murashige and Skoog salt (½ MS) medium (Murashige and Skoog, 1962) containing B5 Vitamins (Gamborg et al., 1968), 5 g/L sucrose, 0.5 g/L 2-(4-morpholino)ethanesulfonic acid (MES) and 2.2 g/L phytagel (Sigma), pH 5.6, with the radicals in contact with the medium, and cultured in a tissue culture room, at 25° C.±2° C. in a 16 h light (100 µmol/m$^2$S)/8 h dark cycle.

Media:
The media used in the present invention are as follows.
Medium I (Basal Medium):
MS major salts, MS minor salts and B5 vitamins, 10 mg/L citric acid, 150 mg/L glutamine, 100 mg/L casein enzymatic hydrolysate, 3% (w/v) sucrose, 0.5 g/L $MgCl_2$ (only used in phytagel-containing medium) in combination with plant growth regulators was used. Medium I was adjusted to pH 5.8-6.0 with 1 N KOH, solidified with 2.5 g/L phytagel and autoclaved at 121° C. for 20 min. All plant growth regulators were filter sterilized before being added to autoclaved medium.

Co-Cultivation Medium:
basal medium plus 20 mg/L acetosyringone (AS), 0.5 g/L MES, 1.5 mg/L 6-benzylaminopurine (6-BA) and 0.05 mg/L 1-naphthaleneacetic acid (NAA), pH 5.0-5.2.

Callus Formation Medium:
basal medium plus 1.5 mg/L 6-BA, 0.05 mg/L NAA, 3.5 mg/L hygromycin (hyg, A.G scientific, SanDiego, Calif.) as selective agent for plant transformation or 1 mg/L glufosinate ammonium (BASTA, Crescent Chemical, NY) and 100 mg/L cefotaxinme (Cef) for elimination of Agrobacteria cells.

Shoot Regeneration Medium I:
basal medium plus 1.5 mg/L 6-BA, 0.05 mg/L 3-indolebutyric acid (IBA), 2 mg/L adenine (adenine hemisulfate salt, SIGMA), 3.5 mg/L Hyg or 1 mg/L glufosinate ammonium and Cef 100 mg/L.

Shoot Regeneration Medium II:
basal medium plus 1.5 mg/L 6-BA, 0.05 mg/L IBA, 0.5 mg/L gibberellic acid ($GA_3$), 4 mg/L Hyg or 1 mg/L glufosinate ammonium and 100 mg/L Cef 100, change phytagel to 7 g/L agar.

Shoot Regeneration Medium III:
basal medium plus 1.5 mg/L 6-BA, 0.05 mg/L IBA, 3.5 mg/L Hyg or 1 mg/L glufosinate ammonium and 100 mg/L Cef.

Shoot Elongation Medium:
basal medium plus 0.3 mg/L 6-BA, 0.1 mg/L $GA_3$, change phytagel to 7 g/L agar.

Rooting Medium:
MS major salts, MS minor salts and B5 vitamins, 3% sucrose, 0.5 g/L MES, 0.07 mg/L IBA, 2.2 g/L phytagel, pH5.6.

Medium II:
liquid MS medium supplemented with 10 g/L glucose, 0.5 g/L MES, 20 mg/L AS, 1.5 mg/L 6-BA, 0.1 mg/L NAA, pH 5.0-5.2.

RNA Extraction and Analysis:
Fresh leaf or seed tissue (100 mg) was ground in liquid nitrogen and extracted with plant RNA purification reagent (Invitrogen). RNA concentration was measured by Nanodrop (Thermo, USA). DNase treatment and reverse transcription (RT) reaction were performed as described (Qu et al., 2007).

Agrobacterium Strain and Vectors:
J. curcas WRINKLE1 (JcWRI1) and DGAT1 sequences were identified by sequencing a Jatropha seed cDNA library. The JcWRI1 full-length cDNA was amplified from J. curcas seed first stranded cDNA product with two primers 5'-AATC GGATCCTAATGAAGAGGTCTTCTGCT-3' (SEQ ID NO:1) and 5'-TCATGTTAATTAATCAAACAG-AATAGTTACAAGAAA-3' (SEQ ID NO:2) (underlined nts are enzyme recognition sites). The PCR product was further inserted into the pBA002-MYC vector treated with the BamHI and PacI to form pBA002-MYC-JcWRI1. The JcDGAT1 full-length cDNA was amplified from J. curcas seed first stranded cDNA product with two primers 5'-CAATA TCTAGACCATGACGATTTTGGAGACCACT-3' (SEQ ID NO:3) and 5'-TATTAGATCTGGTCTTAATTCA-GCATTGCC-3' (SEQ ID NO:4) (underlined nts are enzyme recognition sites). The PCR product was further inserted into the pBA002-HA vector treated with XbaI and BamHI to form pBA002-JcDGAT1-HA. The RcFAH12 full-length cDNA was amplified from castor bean seed first stranded cDNA product with two primers: 5'-CAATA TCTAGACCATGGGAGGTGGTGGTC-3' (SEQ ID NO:5) and 5'-TGTAGGATCCGGATACTTGTTCCGGTACCAG-3' (SEQ ID NO:6) (underlined nts are enzyme recognition sites). The PCR product was further inserted into the pBA002-HA vector treated with XbaI and BamHI to form pBA002-RcFAH12-HA. Vectors were introduced into *Agrobacterium* strain AGL1 by electroporation (BIO-RAD, CA, USA). Transformed *Agrobacterium* cells were used to inoculate liquid LB medium supplemented with 50 mg/L kanamycin (for pCAMBIA 1300-GFP) or 50 mg/L spectimycin (for pBA002-MYC-WRI1, pBA002-JcDGAT1-HA, pBA002-RcFAH12-HA) and 100 mg/L carbicillin and were grown overnight at 28° C., 250 rpm to a final $OD_{595}$=0.7-1. *Agrobacterium* cells were collected by centrifugation at 4200 rpm for 10 min at 20° C. The cell pellet was re-suspended with Medium II and adjusted to an $OD_{595}$ of 0.25-0.35 (only *Agrobacterium* AGL1) prior to co-cultivation.

Isolation of DNA from *J. curcas* Leaves and Genotype Analysis:

Fifty mg of fresh *J. curcas* leaves were disrupted in liquid nitrogen and incubated at 65° C. for one hour after addition of 400 μL CTAB extraction buffer (100 mM Tris, pH 8.0; 1.4 M NaCl; 20 mM EDTA; 2% cetyl trimethylammonium bromide (CTAB)). After two times extraction with chilled-chloroform, DNA was precipitated with isoprepanol and collected by centrifugation. For hygromycin gene genotyping, the primers used were hyg5: 5'-CGATGTAGGAGGGCGTGG-3' (SEQ ID NO:7), hyg3: 5'-ACTTCTACACAGCCATCGGT CC-3' (SEQ ID NO:8). For bar gene genotyping, the primers used were bar5: 5'-GTCTGCAC CATCGTCAACC-3' (SEQ ID NO:9), bar3: 5'-GAAGTCCAGCTGCCAGAAAC-3' (SEQ ID NO:10).

Antibodies and Protein Gel Blot Analysis:

Curcin protein antibody was prepared by Dr. Yin Zhongcao's lab. Western blot analysis was performed as previously described (Qu et al., 2007). Total plant proteins were separated by 12% sodium dodecyl sulfate-polyacrylamide gel electrophoresis. ECL peroxidase conjugated donkey anti-rabbit immunoglobulin G was used as a secondary antibody. Immunoreactive bands were visualized using ECL Western blotting Detection Reagents (GE healthcare).

Example 2

*J. curcas* Cotyledon Explant Transformation

Figure 2:
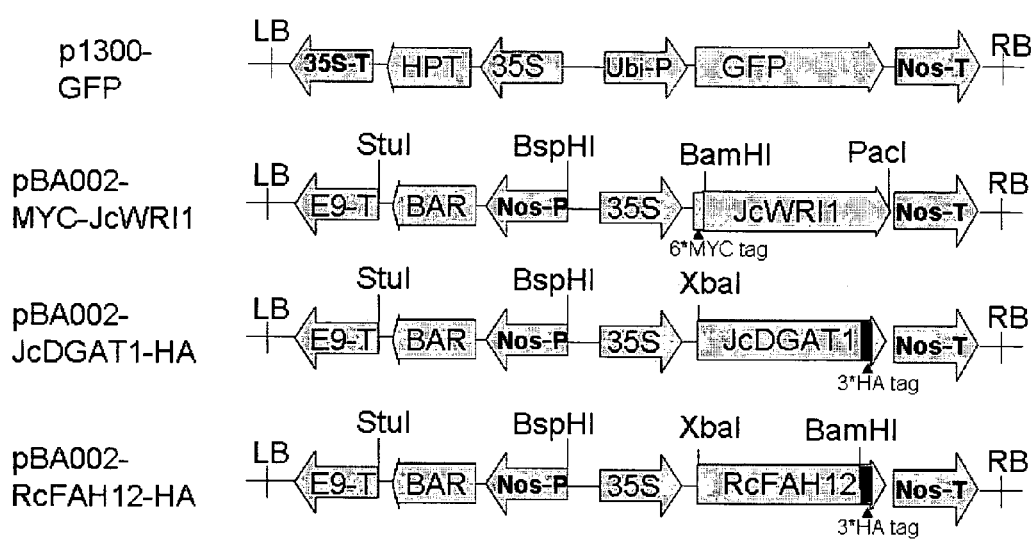
FIG. 2 illustrates *Agrobacterium* transformation vectors utilized to demonstrate the transformation method of the present invention.

FIG. 1 illustrates the *Agrobacterium*-mediated *Jatropha* transformation method as set forth in further detail in this Example. FIG. 2 illustrates the *Agrobacterium* transformation vectors that were used in this Example.

Figure 3:
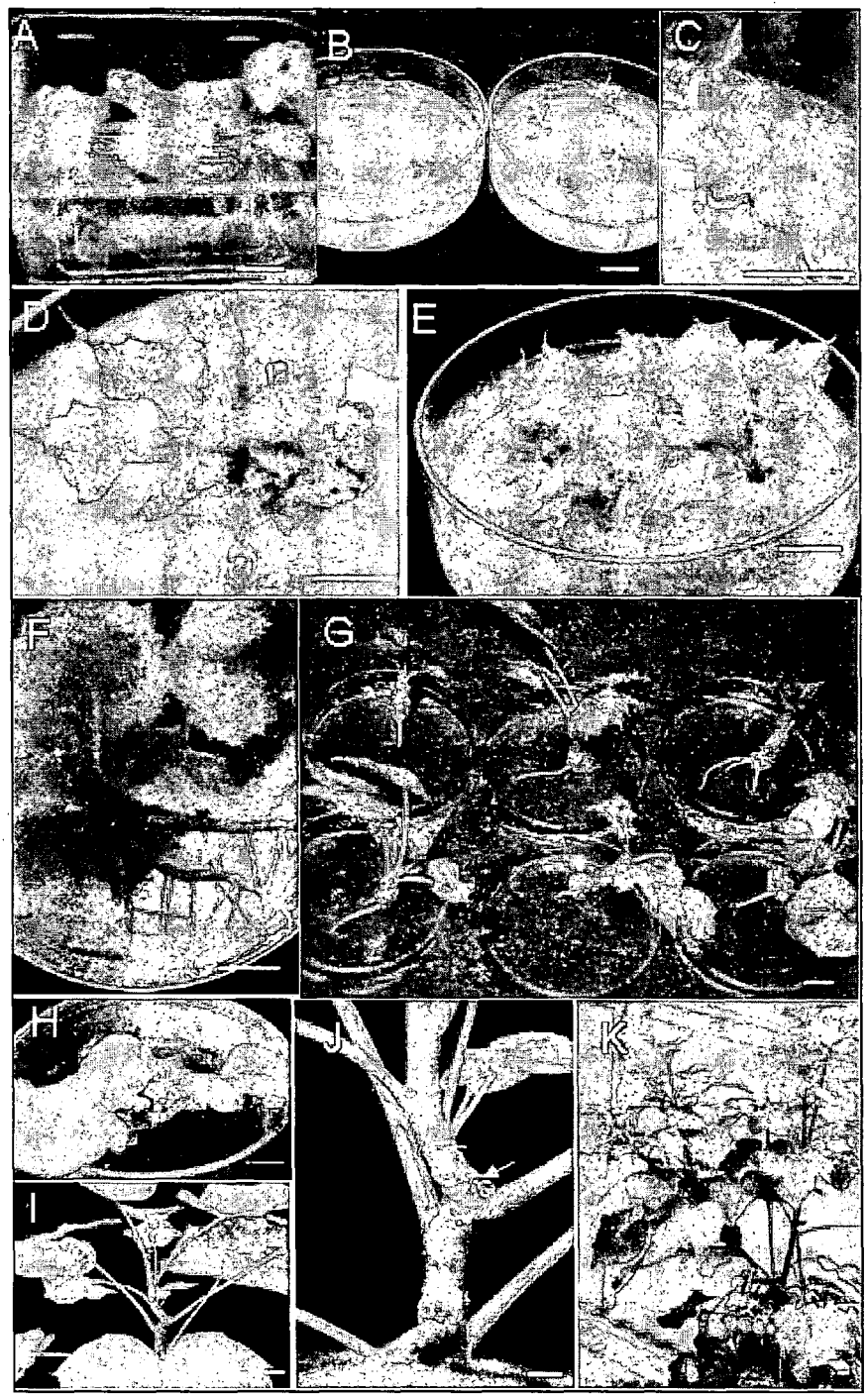
FIGS. 3A-3K show the transformation, regeneration, flowering and seedling of *J. curcas*.

Co-Cultivation:

Cotyledons from 5-7 day old seedlings (Example 1; FIG. 3A) were cut into small pieces (5×5 mm) and incubated with *Agrobacterium* cells (Example 1) harboring the target expression cassette in 20 ml of medium II for 10-20 min at 25° C. Explants were then transferred to the co-cultivation medium for 2-3 days at 22° C. in the dark. Following co-cultivation, explants were rinsed several times with sterile water, following one wash with 300 mg/L cefotaxine. Cotyledon tissues were blotted dry by putting them on a pad of sterilized paper to remove excess surface water.

Selection of Hygromycin-Resistant or Glufosinate Ammonium-Resistant Calli:

After co-cultivation, the explants were plated onto the callus formation medium plate and transferred to darkness at 25° C.±1° C. for three weeks. The nontransformed and transformed explants form callus tissue (FIG. 3B) and some form callus upon culturing (FIG. 3B, right panel; FIG. 3C). Nontransformed explants normally will turn brown when cultured in the dark.

Shoot Regeneration:

Explants with newly emerged hygromycin-resistant or glufosinate ammonium-resistant callus were transferred onto the shoot regeneration medium I for 3 weeks at 25° C. with 16 h light (100 μmol/m$^2$S$^1$)/8 h dark cycles. The methods described here are based on direct shoot induction from transformed callus by adding adenine. While the term "regeneration" is used here to describe the re-creation of a whole plant from such transformed calli. Although 6-BA (6-benzyladenine) has similar effect on shoot regeneration, it can not be used in this special step during the methods described here. Furthermore, higher or lower concentration, early adding or later adding adenine will make the shoot regeneration more difficult or unnormal shooting. In an alternative embodiment, the method for obtaining shoot regeneration involves adding 2 mg/L plus normal 6-BA or other adenine derivative such as 2-isopentenyl adenine. During this period, any shoots regenerated from calli (about 40-50%) were transferred to the shoot regeneration medium II (FIG. 3D). Calli with no regenerated shoots were transferred to the shoot regeneration medium III for further culturing and regeneration of shoots.

Shoot Elongation:

After 4 weeks, regenerated shoots were transferred onto shoot elongation medium for elongation and bud multiplication (FIG. 3E).

Rooting:

The elongated shoots about 2.5 cm in length were rooted in rooting medium (FIG. 3F). Normally it takes more than one month to get roots such as shown in FIG. 3F. Our rooting protocol can provide high rooting efficacy about 45% (FIG. 3G) and one main root length longer than 10 mm can be successfully transferred into soil and get more than 90% live (FIG. 3H).

Grafting:

Elongated, transgenic shoots can also be used as scions for grafting onto non-transgenic root stocks. Healthy and vigorously growing *J. curcas* plants were chosen to be rootstocks. Both scions and rootstocks were cut into the cambium region so that phloem tissues from both will connect after joining. The graft joint was wrapped with parafilm and secured by a tape. Grafted *J. curcas* plants were maintained under low light intensity (28° C. with 16 h light (50 μmol/m$^2$S$^1$)/8 h dark cycles) and 85% humidity for 7 days. Transgenic *J. curcas* shoots grafted onto non-transgenic root stock are shown in FIGS. 3I and 3J. Transgenic *J. curcas* plant showed normal flowering and seeding in greenhouse (FIG. 3K).

Example 3

Transformation and Analysis of Transgenic *J. curcas*

Examples of *Jatropha* transformation and regeneration of BASTA or hygmycin plants from the transformed cells using the method of the present invention are detailed below. Briefly, the method requires that a heterologous DNA construct comprising a plant promoter, a DNA sequence encoding a protein that confers a selective advantage, such as BASTA or hygromycin tolerance, and a 3' untranslated transcriptional terminator region be provided. The DNA constructs comprise a plant promoter operably connected to a DNA coding region encoding a protein that confers BASTA or hygromycin tolerance, and a 3' termination signal. Preferably, the DNA construct encodes an additional gene of interest. For example, the DNA construct may include a gene the expression of which results in increased yields or altered fatty acid content in transformed plants.

In the example below, hygromycin tolerant *Jatropha* plants expressing green fluorescent protein (GFP) were obtained from tissue that was transformed with DNA constructs that included a GFP gene. This GFP gene and other genes such as GUS, luciferase gene, which can serve as easily screenable markers, were used in some of the examples described below, simply because their phenotypes can be readily detected in the transformed plants. It is reasonable to expect that by using DNA constructs created by standard molecular biological techniques, the present invention may be employed to obtain a *Jatropha* plants expressing virtually any other gene. In an alternative embodiment, the method for obtaining transformed *Jatropha* plants involves the cotransformation of two DNA constructs, one of which comprises a selectable marker, such as a BASTA or hygromycin tolerance marker, and the other of which comprises a gene of interest.

Figure 4:
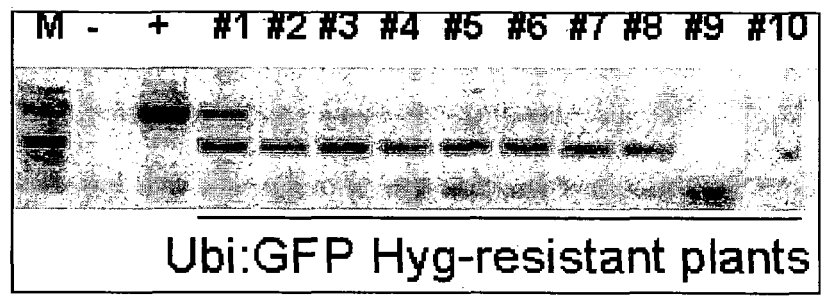
FIG. 4 shows PCR analyse of hyg-resistant ubi:GFP *J. curcas* plants. Lane −: wildtype *Jatropha* control; Lane +: plasmid DNA of p1300-GFP; Lanes #1-#10 from hygromycin-resistant *Jatropha* shoot leaves.
Figure 5:
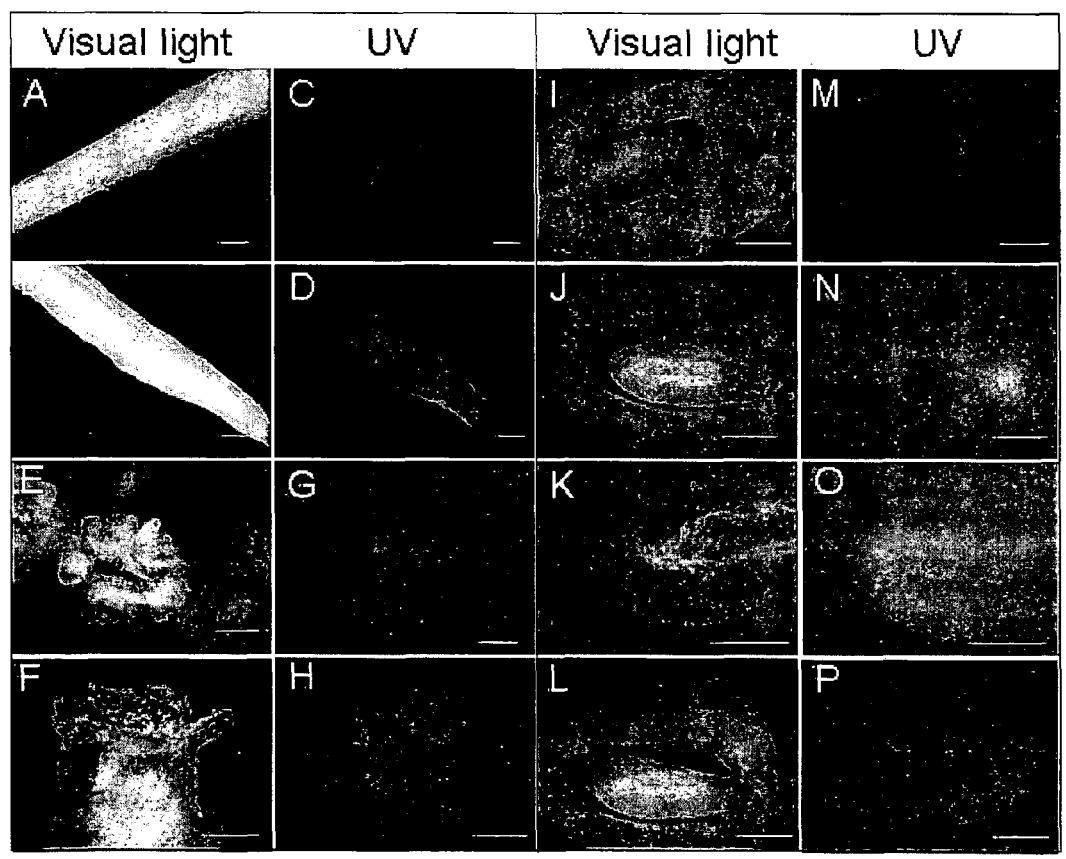

The transformation and shoot regeneration of hygromycin resistant putative GFP transgenic *Jatropha* plants was accomplished according to the method described in Example 2. Genomic DNA of hygromycin resistant shoots was extracted with the method described in Example 1. Genotyping was performed with the hygromycin gene primer pair (SEQ ID NO:7 and SEQ ID NO:8). Nine of 10 events were PCR positive, while the non-transformation control shows no band in the CK lane (FIG. 4). GFP expression was fast screened when transgenic *Jatropha* roots were excited with ultraviolet light (FIG. 3B). The fluorescence indicated that this new introduced GFP expression cassette was expressed in $T_0$ *Jatropha* plants. After ubi:GFP transgenic *Jatropha* flowering, we checked the GFP expression in the inflorescence. The male flower, especially the pollen has some weak green fluoresce (FIG. 5H). We also checked GFP expression in the 3 week after fertilization seeds. Strong GFP expression can be seen in the whole transgenic $T_1$ seed both from outside (FIG. 5N, FIG. 5O) or inside (FIG. 5P). This indicates GFP also express well in the progeny seeds in transgenic *Jatropha*.

Triacylglycerols (TAG) is the main energy storage form after the plant converts solar energy into chemical energy. But the standard biochemical route for its synthesis was thought to be quite wasteful when plants use a variation of glycolysis as an intermediate. WRINKLED1 (WRI1), a transcription factor of the AP2/EREB family, has an impact on more specific aspects of the seed storage process especially transcriptional control conversion of sugar variants into TAG, and therefore, shows a very important role in control seed oil content. Expression of the *Arabidopsis* WRI1 cDNA under the control of the cauliflower mosaic virus 35S-promoter led to increased 10-20% seed oil content. Moreover, the ectopic expression of the WRINKLED1 cDNA caused the accumulation of triacylglycerols in developing seedlings (Cernac and Benning, 2004). We proposed that ectopic expression of *Jatropha* WRI1 gene in *Jatropha* would lead to higher oil content. In addition, the transgenic seedling can develop into embryos or embryo-like organ producing oil when fed with sugars, just like a lipid reactor that can be supplied with sugar-containing liquid substrate for the constitutive CaMV 35S promoter-driven to WRI1 strong expression in vegetative organs.

Figure 6:
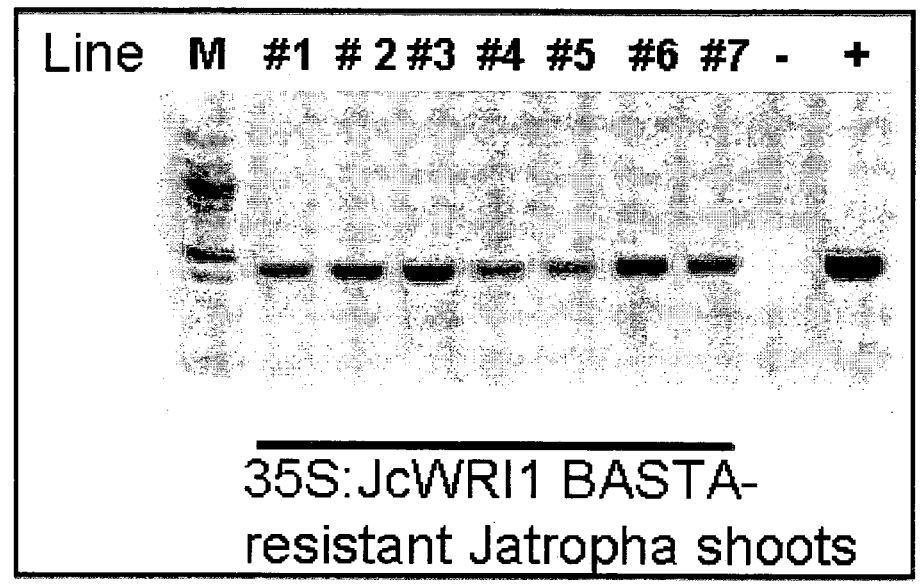
FIG. 6 shows PCR analyses of BASTA-resistant 35S:JcWRI1 *J. curcas* plants. Lane M, DNA ladder; Lane #1-#7 from BASTA-resistant *Jatropha* shoot leaves; lane −, wildtype control; lane +, plasmid DNA of pBA002-MYC-JcWRI1.

We cloned the full-length cDNA of *Jatropha* WRI1 (JcWRI1) PCR amplified from *Jatropha* seed RT-PCR products using PCR primers (SEQ ID NO:1 and SEQ ID NO:2) for the JcWRI1 clone sequence derived from the *Jatropha* seeds cDNA library sequencing. The full length JcWRI1 cDNA sequence is set forth in SEQ ID NO:11. The overexpression vector (pBA002-MYC-JcWRI1) having the JcWRI1 cDNA under the control of CaMV 35S promoter was constructed and transformed into the *Agrobacterium* AGL1 strain. The proposed 6×MYC tag fusion WRI1 could be detected with MYC tag antibody. Transformation and shoot regeneration of BASTA resistant putative JcWRI1 overexpression transgenic *Jatropha* plants was accomplished according to the method described in Example 2. Genomic DNA of hygmycin resistant shoots was extracted with the method described in Example 1. Genotyping was performed with the BASTA gene primer pair (SEQ ID NO:9 and SEQ ID NO:10). All events we tested were PCR positive, while the non-transformation control showed no band in the CK (FIG. 6).

Plant and animal diacylglycerol acyltransferases (DGAT) are responsible for packaging of nascent fatty acids into TAGs, which subsequently accumulate in oil bodies that bud off from the endoplasmic reticulum. Plant type 1 DGAT (DGAT1) genes have been shown to contribute significantly to seed oil content, both by overexpression and through mutational downregulation studies (Zou et al., 2999; Jako et al., 2001). We proposed that ectopic expression of *Jatropha* DGAT1 gene in *Jatropha* would leads to higher level oil content.

Figure 7:
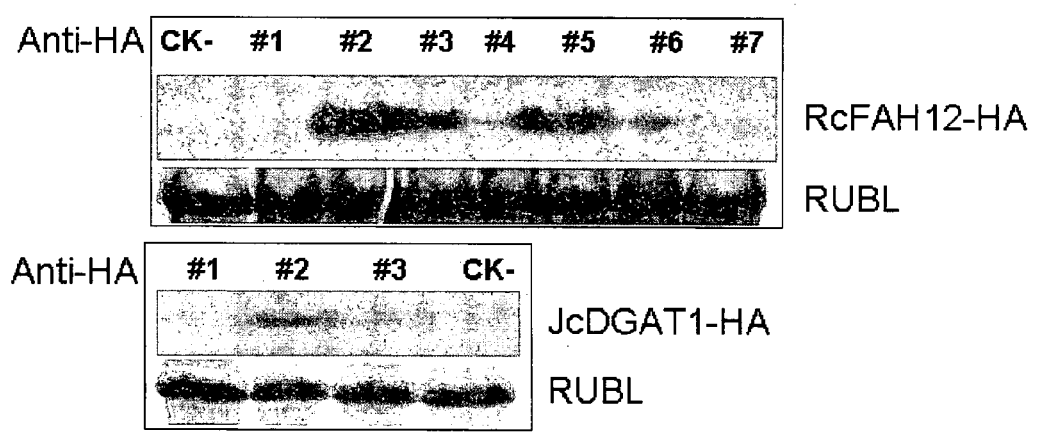
FIG. 7 shows Western blot analysis of RcFAH12 and JcDGAT1 levels in leaves of transgenic *Jatropha* plants expressing 35S:RcFAH12 and 35S:JcDGAT1 using anti-HA antibody. Bottom panel: Coomassie Bright Blue staining of the RUBL (the large subunit of RUBISCO) which serves as a loading control.

We cloned the full-length *Jatropha* DGAT1 cDNA from *Jatropha* seed RT-PCR products using PCR primers (SEQ ID NO:3 and SEQ ID NO:4) according to the DGAT1 clone sequence. The full length JcDGAT1 cDNA sequence is set forth in SEQ ID NO:13. The overexpression vector (pBA002-JcDGAT1-HA) having the JcDGAT1 cDNA under the control of CaMV 35S promoter was constructed and transformed into the *Agrobacterium* AGL1 strain. The proposed 3×HA tag fusion DGAT1 could be detected with HA tag antibody. Transformation and shoot regeneration of BASTA resistant putative JcDGAT1 transgenic *Jatropha* plants was accomplished according to the method described in Example 2. 35S-JcDGAT1 expression was proved by Western blot based on HA-antibody with the method describing in Example 1 (FIG. 7). HA-specific band can be seen in two lanes out of three transgenic *Jatropha* lines.

Plant oils (and their derivatives) can be used in numerous cases and applications for plant-derived industrial feedstocks. When compared with non-renewable petroleum, the renewable nature making them especially attractive for many industrial applications for total loss applications where environmental concerns are an issue. Castor (*Ricinus communis*) oil has numerous applications in transportation, cosmetics and pharmaceuticals, and manufacturing industries. Castor oil contains more than 90% ricinoleic acid, which is a monounsaturated, 18-carbon fatty acid. It is unusual in that it has a hydroxyl functional group on the twelfth carbon. This functional group causes ricinoleic acid (and castor oil) to be unusually polar (http colon en dot wikipedia dot org slash wiki slash Castor_oil). One specific enzyme: fatty acid hydroxylase 12 (FAH12) is responsible for adding the hydroxyl group instead of normal FAD2 function to introduce unsaturated band on the twelfth carbon (van de Loo et al., 1995). Compared to other seed oils which lack the hydroxyl group, castor oil demands a higher price. Despite a widespread demand for castor oil, however, cultivation of this crop is restricted due to the presence of a toxin (ricin) and allergenic proteins, and thus the cost of castor oil is relatively high. Transgenic exogenous FAH12 can produce hydroxyl-castor oil in *Arabidopsis* seeds (Lu et al., 2006). We proposed that ectopic expression of castor bean FAH12 gene in *Jatropha* would lead to the production of castor oil.

We cloned the full-length castor bean FAH12 cDNA (RcFAH12) from castor bean seed RT-PCR products using PCR primers (SEQ ID NO:5 and SEQ ID NO:6) according to the FAH12 CDS sequence. The full length RcFAH12 cDNA sequence is set forth in SEQ ID NO:15. The overexpression vector (pBA002-RcFAH12-HA) having the RcFAH12 cDNA under the control of CaMV 35S promoter was constructed and transformed into the *Agrobacterium* AGL1 strain. The proposed 3×HA tag fusion RcFAH12 could be detected with HA tag antibody. Transformation and shoot regeneration of BASTA resistant putative RcFAH12 transgenic *Jatropha* plants was accomplished according to the method described in Example 2. 35S-RcFAH12 expression was proved by Western blot based on HA-antibody with the method describing in Example 1. HA-specific band can be seen in 5 lanes out of 7 transgenic *Jatropha* lines (FIG. 7). Two lines, #2 and #5, have very high FAH12-HA fusion expression protein level.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Cernac, A. and Benning, C. (2004). WRINKLED1 encodes an AP2/EREB domain protein involved in the control of storage compound biosynthesis in *Arabidopsis*. *Plant J* 40:575-585.

Gamborg, O. L. et al. (1968). Nutrient requirements of suspension cultures of soybean root cells. *Exp Cell Res* 50:151-158.

Jako, C. et al. (2001). Seed-specific over-expression of an *Arabidopsis* cDNA encoding a diacylglycerol acyltransferase enhances seed oil content and seed weight. *Plant Physiol* 126:861-874.

Jones, N. M. J. (1991). *Jatropha curcas*—a multipurpose species for problematic sites. *Land Resources Series* 1:1-12.

Li, M. L. H. et al. (2008). Establishment of an *Agrobacterium*-mediated cotyledon disc transformation method for *Jatropha curcas*. *Plant Cell Tiss Org Cult* 92:173-181.

Lu, C. et al. (2006). A high-throughput screen for genes from castor that boost hydroxy fatty acid accumulation in seed oils of transgenic *Arabidopsis*. *Plant J* 45:847-856.

Murashige, T. and Skoog, F. (1962). A revised medium for rapid growth and bioassays with tobacco tissue cultures. *Physiol Plant* 15:473-497.

Narayana, D. S. A et al. (2007). Distinct Begomoviruses Closely Related to Cassava Mosaic Viruses cause Indian *Jatropha* Mosaic Disease. *Int'l J Virol* 3:1-11.

Qu, J. et al. (2007). Artificial microRNA-mediated virus resistance in plants. *J Virol* 81:6690-6699.

Sujatha, M. et al. (2008). Role of biotechnological interventions in the improvement of castor (*Ricinus communis* L.) and *Jatropha curcas* L. *Biotechnol Adv* 26:424-435.

van de Loo, F. J. et al. (1995). An oleate 12-hydroxylase from *Ricinus communis* L. is a fatty acyl desaturase homolog. *Proc Natl Acad Sci USA* 92:6743-6747.

Zou, J. et al. (1999). The *Arabidopsis thaliana* TAG1 mutant has a mutation in a diacylglycerol acyltransferase gene. *Plant J* 19:645-653.

What is claimed is:

1. A method for regenerating plants of *Jatropha curcas* comprising:
   (a) culturing cotyledon explants on a solid callus formation medium which comprises MS mineral salts, B5 vitamins, citric acid, glutamine, casein hydrolysate, sucrose, 6-benzylaminopurine (6-BA) and 1-naphthaleneacetic acid (NAA) for a period of time to produce explants with callus tissue;
   (b) culturing the callus tissue on a solid first shoot regeneration medium which comprises MS mineral salts, B5 vitamins, citric acid, glutamine, casein hydrolysate, sucrose, adenine, 6-BA and 3-indolebutyric acid (IBA) for a period of time to produce callus tissue with shoots and callus tissue;
   (c) culturing the shoots on a solid second shoot regeneration medium which comprises MS mineral salts, B5 vitamins, citric acid, glutamine, casein hydrolysate, sucrose, 6-BA, IBA and gibberellic acid ($GA_3$) for a period of time to produce shoots;
   (d) culturing shoots from step (c) on a solid shoot elongation medium which comprises MS mineral salts, B5 vitamins, citric acid, glutamine, casein hydrolysate, sucrose, 6-BA and $GA_3$ for a period of time to produce elongated shoots; and
   (e) rooting or grafting the elongated shoots, wherein rooting is performed by culturing the elongated shoots on a solid rooting medium which comprises MS mineral salts, B5 vitamins, sucrose and IBA for a period of time to produce plantlets or wherein grafting is performed by grafting the elongated shoots to *J. curcas* rootstock.

2. The method of claim 1, which further comprising culturing the callus tissue from step (b) on a solid third shoot regeneration medium which comprises MS mineral salts, B5 vitamins, citric acid, glutamine, casein hydrolysate, sucrose, 6-BA and IBA for a period of time to produce callus tissue with shoots which is then cultured in step (c).

3. The method of claim 1, wherein the concentration of media components are:
   (a) citric acid: about 10 mg/L to about 30 mg/L, preferably about 10 mg/L; glutamine: about 150 mg/L to about 200 mg/L, preferably about 150 mg/L; casein hydrolysate: about 100 mg/L; sucrose: about 3% w/v; 6-BA: about 1.5 mg/L; and NAA: is about 0.05 mg/L to about 0.1 mg/L, preferably about 0.05 mg/L in the callus formation medium;
   (b) citric acid: about 10 mg/L to about 30 mg/L, preferably about 10 mg/L; glutamine: about 150 mg/L to about 200 mg/L, preferably about 150 mg/L; casein hydrolysate: about 100 mg/L; sucrose: about 3% w/v; adenine: about 2 mg/L to about 4 mg/L, preferably about 2 mg/L; 6-BA: about 1.5 mg/L; and IBA: about 0.05 mg/L in the first shoot regeneration medium;
   (c) citric acid: about 10 mg/L to about 30 mg/L, preferably about 10 mg/L; glutamine: about 150 mg/L to about 200 mg/L, preferably about 150 mg/L; casein hydrolysate: about 100 mg/L; sucrose: about 3% w/v; 6-BA: about 1.5 mg/L; IBA: about 0.05 mg/L and $GA_3$: about 0.05 mg/L to about 0.5 mg/L, preferably about 0.5 mg/L in the second shoot regeneration medium;
   (d) citric acid: about 10 mg/L to about 30 mg/L, preferably about 10 mg/L; glutamine: about 150 mg/L to about 200 mg/L, preferably about 150 mg/L; casein hydrolysate: about 100 mg/L; sucrose: about 3% w/v; 6-BA: about 0.3 mg/L; and $GA_3$: about 0.1 mg/L to about 0.5 mg/L, preferably about 0.1 mg/L in the shoot elongation medium; and
   (e) sucrose: about 3% w/v and IBA: is about 0.07 g/L in the rooting medium.

4. The method of claim 2, wherein the concentration of the media components in the third shoot regeneration medium are citric acid: about 10 mg/L to about 30 mg/L, preferably about 10 mg/L; glutamine: about 150 mg/L to about 200 mg/L, preferably about 150 mg/L; casein hydrolysate: about 100 mg/L; sucrose: about 3% w/v; 6-BA: about 1.5 mg/L; and IBA: about 0.05 mg/L.

5. The method of claim 1, wherein periods of time for the culturing are:
   (a) about two weeks to about three weeks on the callus formation;
   (b) about three weeks to about four weeks on the first shoot regeneration medium;
   (c) about three weeks to about four weeks on the second shoot regeneration medium;
   (d) about two weeks to about three weeks on the shoot elongation medium; and
   (e) about three weeks to about four weeks on the rooting medium.

6. The method of claim 2, wherein the period of time for culturing on the third shoot regeneration medium is about four weeks to about five weeks, preferably about four weeks.

7. The method of claim 5, wherein the periods of time for the culturing are:
   (a) about three weeks on the callus formation;
   (b) about three weeks on the first shoot regeneration medium;
   (c) about four weeks on the second shoot regeneration medium;
   (d) about two weeks on the shoot elongation medium; and
   (e) about four weeks on the rooting medium.

8. The method of claim 4, wherein the period of time for culturing on the third shoot regeneration medium is about four weeks to about five weeks, preferably about four weeks.

9. A method for *Agrobacterium*-mediated transformation of plants of *Jatropha curcas* comprising:
   (a) co-culturing cotyledon explants with Agrobacterium on a solid medium which comprises MS mineral salts, B5 vitamins, citric acid, glutamine, casein hydrolysate, sucrose, acetospringone (AS), 6-benzylaminopurine (6-BA) and 1-naphthaleneacetic acid (NAA) for a period of time to produce transformed cotyledon explants
   (b) culturing transformed cotyledon explants on a solid callus formation medium which comprises MS mineral salts, B5 vitamins, citric acid, glutamine, casein hydrolysate, sucrose, 6-BA, NAA, a selective agent and an *Agrobacterium* eradicant in the dark for a period of time to produce explants with transformed callus tissue;
   (c) culturing the transformed callus tissue on a solid first shoot regeneration medium which comprises MS mineral salts, B5 vitamins, citric acid, glutamine, casein hydrolysate, sucrose, adenine, 6-BA, 3-indolebutyric acid (IBA), a selective agent and an Agrobacterium eradicant for a period of time to produce transformed callus tissue with transformed shoots and transformed callus tissue;
   (d) culturing the transformed shoots on a solid second shoot regeneration medium which comprises MS mineral salts, B5 vitamins, citric acid, glutamine, casein hydrolysate, sucrose, 6-BA, IBA, gibberellic acid ($GA_3$), a selective agent and an *Agrobacterium* eradicant for a period of time to produce transformed shoots;
   (e) culturing transformed shoots from step (c) on a solid shoot elongation medium which comprises MS mineral salts, B5 vitamins, citric acid, glutamine, casein hydrolysate, sucrose, 6-BA and $GA_3$ for a period of time to produce elongated transformed shoots; and
   (f) rooting or grafting the elongated transformed shoots, wherein rooting is performed by culturing the elongated transformed shoots on a solid rooting medium which comprises MS mineral salts, B5 vitamins, sucrose and IBA for a period of time to produce transformed plantlets or wherein grafting is performed by grafting the elongated transformed shoots to *J. curcas* rootstock.

10. The method of claim 9, which further comprising culturing the transformed callus tissue from step (c) on a solid third shoot regeneration medium which comprises MS mineral salts, B5 vitamins, citric acid, glutamine, casein hydrolysate, sucrose, 6-BA, IBA a selective agent and an *Agrobacterium* eradicant for a period of time to produce callus tissue with shoots which is then cultured in step (d).

11. The method of claim 9, wherein the concentration of media components are:
   (a) citric acid: about 10 mg/L to about 30 mg/L, preferably about 10 mg/L; glutamine: about 150 mg/L to about 200 mg/L, preferably about 150 mg/L; casein hydrolysate: about 100 mg/L; sucrose: about 3% w/v; AS: about 20 mg/L; 6-BA: 1.5 mg/L; and NAA: is about 0.05 mg/L to about 0.1 mg/L, preferably about 0.05 mg/L in the co-culturing medium;
   (b) citric acid: about 10 mg/L to about 30 mg/L, preferably about 10 mg/L; glutamine: about 150 mg/L to about 200 mg/L, preferably about 150 mg/L; casein hydrolysate: about 100 mg/L; sucrose: about 3% w/v; 6-BA: about 1.5 mg/L; and NAA: is about 0.05 mg/L to about 0.1 mg/L, preferably about 0.05 mg/L in the callus formation medium;
   (c) citric acid: about 10 mg/L to about 30 mg/L, preferably about 10 mg/L; glutamine: about 150 mg/L to about 200 mg/L, preferably about 150 mg/L; casein hydrolysate: about 100 mg/L; sucrose: about 3% w/v; adenine: about 2 mg/L to about 4 mg/L, preferably about 2 mg/L; 6-BA: about 1.5 mg/L; and IBA: about 0.05 mg/L in the first shoot regeneration medium;
   (d) citric acid: about 10 mg/L to about 30 mg/L, preferably about 10 mg/L; glutamine: about 150 mg/L to about 200 mg/L, preferably about 150 mg/L; casein hydrolysate: about 100 mg/L; sucrose: about 3% w/v; 6-BA: about 1.5 mg/L; IBA: about 0.05 mg/L and $GA_3$: about 0.05 mg/L to about 0.5 mg/L, preferably about 0.5 mg/L in the second shoot regeneration medium;
   (e) citric acid: about 10 mg/L to about 30 mg/L, preferably about 10 mg/L; glutamine: about 150 mg/L to about 200 mg/L, preferably about 150 mg/L; casein hydrolysate: about 100 mg/L; sucrose: about 3% w/v; 6-BA: about 0.3 mg/L; and $GA_3$: about 0.1 mg/L to about 0.5 mg/L, preferably about 0.1 mg/L in the shoot elongation medium; and
   (f) sucrose: about 3% w/v and IBA: is about 0.07 g/L in the rooting medium.

12. The method of claim 10, wherein the concentration of the media components in the third shoot regeneration medium are citric acid: about 10 mg/L to about 30 mg/L, preferably about 10 mg/L; glutamine: about 150 mg/L to about 200 mg/L, preferably about 150 mg/L; casein hydrolysate: about 100 mg/L; sucrose: about 3% w/v; 6-BA: about 1.5 mg/L; and IBA: about 0.05 mg/L.

13. The method of claim 9, wherein the periods of time for the co-culturing or culturing are:
   (a) about 2-3 days;
   (b) about two weeks to about three weeks on the callus formation;
   (c) about three weeks to about four weeks on the first shoot regeneration medium;
   (d) about three weeks to about four weeks on the second shoot regeneration medium;
   (e) about two weeks to about three weekson the shoot elongation medium; and
   (f) on the rooting medium.

14. The method of claim 10, wherein the period of time for culturing on the third shoot regeneration medium is about four weeks to about five weeks, preferably about four weeks.

15. The method of claim 13, wherein the periods of time for the co-culturing or culturing are:
   (a) about 2-3 days;
   (b) about three weeks on the callus formation;
   (c) about three weeks on the first shoot regeneration medium;
   (d) about four weeks on the second shoot regeneration medium;
   (e) about two weeks on the shoot elongation medium; and
   (f) about four weeks on the rooting medium.

16. The method of claim 12, wherein the period of time for culturing on the third shoot regeneration medium is about four weeks to about five weeks, preferably about four weeks.

* * * * *

SEQUENCE LISTING

<160> NUMBER OF SEQ ID NOS: 16

<210> SEQ ID NO 1
<211> LENGTH: 30
<212> TYPE: DNA
<213> ORGANISM: Jatropha curcas

<400> SEQUENCE: 1
aatcggatcc taatgaagag gtcttctgct                               30

<210> SEQ ID NO 2
<211> LENGTH: 36
<212> TYPE: DNA
<213> ORGANISM: Jatropha curcas

<400> SEQUENCE: 2
tcatgttaat taatcaaaca gaatagttac aagaaa                        36

```
<210> SEQ ID NO 3
<211> LENGTH: 34
<212> TYPE: DNA
<213> ORGANISM: Jatropha curcas

<400> SEQUENCE: 3
caatatctag accatgacga ttttggagac cact                              34

<210> SEQ ID NO 4
<211> LENGTH: 30
<212> TYPE: DNA
<213> ORGANISM: Jatropha curcas

<400> SEQUENCE: 4
tattagatct ggtcttaatt cagcattgcc                                   30

<210> SEQ ID NO 5
<211> LENGTH: 29
<212> TYPE: DNA
<213> ORGANISM: Ricinus communis

<400> SEQUENCE: 5
caatatctag accatgggag gtggtggtc                                    29

<210> SEQ ID NO 6
<211> LENGTH: 31
<212> TYPE: DNA
<213> ORGANISM: Ricinus communis

<400> SEQUENCE: 6
tgtaggatcc ggatacttgt tccggtacca g                                 31

<210> SEQ ID NO 7
<211> LENGTH: 18
<212> TYPE: DNA
<213> ORGANISM: Escherichia coli

<400> SEQUENCE: 7
cgatgtagga gggcgtgg                                                18

<210> SEQ ID NO 8
<211> LENGTH: 22
<212> TYPE: DNA
<213> ORGANISM: Escherichia coli

<400> SEQUENCE: 8
acttctacac agccatcggt cc                                           22

<210> SEQ ID NO 9
<211> LENGTH: 19
<212> TYPE: DNA
<213> ORGANISM: Streptomyces hygroscopicus

<400> SEQUENCE: 9
gtctgcacca tcgtcaacc                                               19

<210> SEQ ID NO 10
<211> LENGTH: 20
<212> TYPE: DNA
<213> ORGANISM: Streptomyces hygroscopicus

<400> SEQUENCE: 10
gaagtccagc tgccagaaac                                              20
```

```
<210> SEQ ID NO 11
<211> LENGTH: 1251
<212> TYPE: DNA
<213> ORGANISM: Jatropha curcas
<220> FEATURE:
<221> NAME/KEY: CDS
<222> LOCATION: (1)..(1251)
<220> FEATURE:
<221> NAME/KEY: misc_feature
<222> LOCATION: (518)..(518)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t

<400> SEQUENCE: 11 atg aag agg tct tct gct tca tct tgc tct tct tct tct tct tct          48
Met Lys Arg Ser Ser Ala Ser Ser Cys Ser Ser Ser Ser Ser Ser
1               5                   10                  15 tct tct cca tcc tct tct tcg tct tct gct tgt tct gct tcg tct tct     96
Ser Ser Pro Ser Ser Ser Ser Ser Ser Ala Cys Ser Ala Ser Ser Ser
            20                  25                  30 tgc tta gat tca gta tct cct cct aat cac cat caa tta cga tca gag    144
Cys Leu Asp Ser Val Ser Pro Pro Asn His His Gln Leu Arg Ser Glu
        35                  40                  45 aaa tca aaa tcc aaa cgc att cga aaa att caa acc aag caa gat aaa    192
Lys Ser Lys Ser Lys Arg Ile Arg Lys Ile Gln Thr Lys Gln Asp Lys
    50                  55                  60 tgt cag act aca gct act acc acc agt cca agc ggc ggc ggt agg aga    240
Cys Gln Thr Thr Ala Thr Thr Thr Ser Pro Ser Gly Gly Gly Arg Arg
65                  70                  75                  80 agc tcc att tac aga gga gtc acc cgg cat aga tgg act gga agg ttt    288
Ser Ser Ile Tyr Arg Gly Val Thr Arg His Arg Trp Thr Gly Arg Phe
                85                  90                  95 gaa gct cat ctt tgg gat aag agt tct tgg aat aac att caa aac aag    336
Glu Ala His Leu Trp Asp Lys Ser Ser Trp Asn Asn Ile Gln Asn Lys
            100                 105                 110 aaa gga agg caa gtt tat ttg ggg gct tac gac aat gag gaa gca gct    384
Lys Gly Arg Gln Val Tyr Leu Gly Ala Tyr Asp Asn Glu Glu Ala Ala
        115                 120                 125 gct cat acc tat gat ctt gct gct ctc aag tac tgg gga caa gac acc    432
Ala His Thr Tyr Asp Leu Ala Ala Leu Lys Tyr Trp Gly Gln Asp Thr
    130                 135                 140 act ttg aat ttt ccg ata gag aca tac tca aag gag ctt gaa gag atg    480
Thr Leu Asn Phe Pro Ile Glu Thr Tyr Ser Lys Glu Leu Glu Glu Met
145                 150                 155                 160 caa aag atg agc aag gaa gag tac tta gca tct ctt cna cga aga agc    528
Gln Lys Met Ser Lys Glu Glu Tyr Leu Ala Ser Leu Xaa Arg Arg Ser
                165                 170                 175 agt gga ttt tca aga gga gtt tct aag tac cgg gga gta gct agg cat    576
Ser Gly Phe Ser Arg Gly Val Ser Lys Tyr Arg Gly Val Ala Arg His
            180                 185                 190 cat cac aat ggc cgg tgg gaa gct cga att ggc cgg gtt ttt ggc aat    624
His His Asn Gly Arg Trp Glu Ala Arg Ile Gly Arg Val Phe Gly Asn
        195                 200                 205 aag tat ctc tac ctc gga act tac aat aca caa gaa gag gca gca gca    672
Lys Tyr Leu Tyr Leu Gly Thr Tyr Asn Thr Gln Glu Glu Ala Ala Ala
    210                 215                 220 tat gat atg gca gca ata gag tac aga gga gca aat gca gta acc aat    720
Tyr Asp Met Ala Ala Ile Glu Tyr Arg Gly Ala Asn Ala Val Thr Asn
225                 230                 235                 240
```

|  |  |  |  |  |  |  |  |  |  |  |  |  |  |  |  |
|---|---|---|---|---|---|---|---|---|---|---|---|---|---|---|---|
| ttt | gat | gtc | agc | cat | tac | ata | gac | cgt | ttg | aag | aag | aaa | ggc | att | cct | 768 |
| Phe | Asp | Val | Ser | His | Tyr | Ile | Asp | Arg | Leu | Lys | Lys | Lys | Gly | Ile | Pro |
|  |  |  |  | 245 |  |  |  |  | 250 |  |  |  |  | 255 |  |

| tta | gat | aaa | atc | cta | cca | gaa | acn | ctt | tct | aaa | ggc | tca | aaa | gag | tca | 816 |
| Leu | Asp | Lys | Ile | Leu | Pro | Glu | Thr | Leu | Ser | Lys | Gly | Ser | Lys | Glu | Ser |
| 260 |  |  |  |  | 265 |  |  |  |  | 270 |  |  |  |  |  |

| gaa | gaa | atc | gag | cga | acc | tca | ccc | tta | ccg | ttg | cca | tca | cca | cca | tca | 864 |
| Glu | Glu | Ile | Glu | Arg | Thr | Ser | Pro | Leu | Pro | Leu | Pro | Ser | Pro | Pro | Ser |
|  |  |  | 275 |  |  |  |  | 280 |  |  |  |  | 285 |  |  |

| cca | tca | ata | aca | cca | tta | cac | gaa | gaa | ata | gtc | tca | cca | cag | ctg | ctt | 912 |
| Pro | Ser | Ile | Thr | Pro | Leu | His | Glu | Glu | Ile | Val | Ser | Pro | Gln | Leu | Leu |
|  | 290 |  |  |  |  | 295 |  |  |  |  | 300 |  |  |  |  |

| gaa | act | gaa | tgc | cca | caa | cat | cct | cca | tgt | atg | gat | act | tgt | act | atg | 960 |
| Glu | Thr | Glu | Cys | Pro | Gln | His | Pro | Pro | Cys | Met | Asp | Thr | Cys | Thr | Met |
| 305 |  |  |  |  | 310 |  |  |  |  | 315 |  |  |  |  | 320 |

| atc | gtt | atg | gac | cct | ata | gaa | gag | cac | gag | ctt | act | tgg | agc | ttc | tgt | 1008 |
| Ile | Val | Met | Asp | Pro | Ile | Glu | Glu | His | Glu | Leu | Thr | Trp | Ser | Phe | Cys |
|  |  |  |  | 325 |  |  |  |  | 330 |  |  |  |  | 335 |  |

| ctc | gat | tcg | ggg | tta | gtt | ccg | ctc | cct | gtg | cct | gac | cta | cca | cta | gca | 1056 |
| Leu | Asp | Ser | Gly | Leu | Val | Pro | Leu | Pro | Val | Pro | Asp | Leu | Pro | Leu | Ala |
|  |  |  | 340 |  |  |  |  | 345 |  |  |  |  | 350 |  |  |

| aat | ggc | tgt | gag | tta | cca | gac | ttg | ttg | gat | gac | aca | ggc | ttt | gaa | gac | 1104 |
| Asn | Gly | Cys | Glu | Leu | Pro | Asp | Leu | Leu | Asp | Asp | Thr | Gly | Phe | Glu | Asp |
|  |  | 355 |  |  |  |  | 360 |  |  |  |  | 365 |  |  |  |

| aat | att | gac | ttg | ata | ttt | gat | gct | tgt | tgc | ttc | gga | aat | gat | gcc | aac | 1152 |
| Asn | Ile | Asp | Leu | Ile | Phe | Asp | Ala | Cys | Cys | Phe | Gly | Asn | Asp | Ala | Asn |
| 370 |  |  |  |  | 375 |  |  |  |  | 380 |  |  |  |  |  |

| cct | gca | gat | gag | aat | ggg | aaa | gag | agg | ttg | tct | tcc | gct | tca | act | tct | 1200 |
| Pro | Ala | Asp | Glu | Asn | Gly | Lys | Glu | Arg | Leu | Ser | Ser | Ala | Ser | Thr | Ser |
| 385 |  |  |  |  | 390 |  |  |  |  | 395 |  |  |  |  | 400 |

| cca | tct | tgt | tcc | aca | aca | tta | act | tct | gtt | tct | tgt | aac | tat | tct | gtt | 1248 |
| Pro | Ser | Cys | Ser | Thr | Thr | Leu | Thr | Ser | Val | Ser | Cys | Asn | Tyr | Ser | Val |
|  |  |  |  | 405 |  |  |  |  | 410 |  |  |  |  | 415 |  |

| tga |  |  |  |  |  |  |  |  |  |  |  |  |  |  |  | 1251 |

<210> SEQ ID NO 12
<211> LENGTH: 416
<212> TYPE: PRT
<213> ORGANISM: Jatropha curcas
<220> FEATURE:
<221> NAME/KEY: misc_feature
<222> LOCATION: (173)..(173)
<223> OTHER INFORMATION: The 'Xaa' at location 173 stands for Gln, Arg,
      Pro, or Leu.

<400> SEQUENCE: 12

Met Lys Arg Ser Ser Ala Ser Ser Cys Ser Ser Ser Ser Ser Ser
1               5                   10                  15

Ser Ser Pro Ser Ser Ser Ser Ser Ala Cys Ser Ala Ser Ser Ser
                20                  25                  30

Cys Leu Asp Ser Val Ser Pro Pro Asn His His Gln Leu Arg Ser Glu
            35                  40                  45

Lys Ser Lys Ser Lys Arg Ile Arg Lys Ile Gln Thr Lys Gln Asp Lys
    50                  55                  60

Cys Gln Thr Thr Ala Thr Thr Thr Ser Pro Ser Gly Gly Gly Arg Arg
65                  70                  75                  80

Ser Ser Ile Tyr Arg Gly Val Thr Arg His Arg Trp Thr Gly Arg Phe
                85                  90                  95

Glu Ala His Leu Trp Asp Lys Ser Ser Trp Asn Asn Ile Gln Asn Lys
            100                 105                 110

-continued

Lys Gly Arg Gln Val Tyr Leu Gly Ala Tyr Asp Asn Glu Glu Ala Ala
            115                 120                 125

Ala His Thr Tyr Asp Leu Ala Ala Leu Lys Tyr Trp Gly Gln Asp Thr
        130                 135                 140

Thr Leu Asn Phe Pro Ile Glu Thr Tyr Ser Lys Glu Leu Glu Glu Met
145                 150                 155                 160

Gln Lys Met Ser Lys Glu Glu Tyr Leu Ala Ser Leu Xaa Arg Arg Ser
                165                 170                 175

Ser Gly Phe Ser Arg Gly Val Ser Lys Tyr Arg Gly Val Ala Arg His
            180                 185                 190

His His Asn Gly Arg Trp Glu Ala Arg Ile Gly Arg Val Phe Gly Asn
        195                 200                 205

Lys Tyr Leu Tyr Leu Gly Thr Tyr Asn Thr Gln Glu Glu Ala Ala Ala
    210                 215                 220

Tyr Asp Met Ala Ala Ile Glu Tyr Arg Gly Ala Asn Ala Val Thr Asn
225                 230                 235                 240

Phe Asp Val Ser His Tyr Ile Asp Arg Leu Lys Lys Gly Ile Pro
                245                 250                 255

Leu Asp Lys Ile Leu Pro Glu Thr Leu Ser Lys Gly Ser Lys Glu Ser
            260                 265                 270

Glu Glu Ile Glu Arg Thr Ser Pro Leu Pro Leu Pro Ser Pro Ser
        275                 280                 285

Pro Ser Ile Thr Pro Leu His Glu Glu Ile Val Ser Pro Gln Leu Leu
290                 295                 300

Glu Thr Glu Cys Pro Gln His Pro Pro Cys Met Asp Thr Cys Thr Met
305                 310                 315                 320

Ile Val Met Asp Pro Ile Glu Glu His Glu Leu Thr Trp Ser Phe Cys
                325                 330                 335

Leu Asp Ser Gly Leu Val Pro Leu Pro Val Pro Asp Leu Pro Leu Ala
            340                 345                 350

Asn Gly Cys Glu Leu Pro Asp Leu Leu Asp Asp Thr Gly Phe Glu Asp
        355                 360                 365

Asn Ile Asp Leu Ile Phe Asp Ala Cys Cys Phe Gly Asn Asp Ala Asn
    370                 375                 380

Pro Ala Asp Glu Asn Gly Lys Glu Arg Leu Ser Ser Ala Ser Thr Ser
385                 390                 395                 400

Pro Ser Cys Ser Thr Thr Leu Thr Ser Val Ser Cys Asn Tyr Ser Val
                405                 410                 415

<210> SEQ ID NO 13
<211> LENGTH: 1566
<212> TYPE: DNA
<213> ORGANISM: Jatropha curcas
<220> FEATURE:
<221> NAME/KEY: CDS
<222> LOCATION: (1)..(1566)

<400> SEQUENCE: 13 atg acg att ttg gag acc act act agc gga ggt gat ggt gtt gct gag    48
Met Thr Ile Leu Glu Thr Thr Thr Ser Gly Gly Asp Gly Val Ala Glu
1               5                  10                  15 tcg tct tcc gat ctt aac gta tcg ctt cga cgg aga cgg aaa ggc acc    96
Ser Ser Ser Asp Leu Asn Val Ser Leu Arg Arg Arg Arg Lys Gly Thr
            20                  25                  30 agc tcg gat gga gct ttg ccg gaa ttg act tcg aat att gtt gaa ttg   144
Ser Ser Asp Gly Ala Leu Pro Glu Leu Thr Ser Asn Ile Val Glu Leu
        35                  40                  45

|     |     |     |     |     |     |     |     |     |     |     |     |     |     |     |     | |
|---|---|---|---|---|---|---|---|---|---|---|---|---|---|---|---|---|
| gaa | tct | gaa | agc | ggt | ggc | cag | gtg | atg | atg | gat | cca | ggt | gtg | gtg | acg | 192 |
| Glu | Ser | Glu | Ser | Gly | Gly | Gln | Val | Met | Met | Asp | Pro | Gly | Val | Val | Thr | |
| 50  |     |     |     | 55  |     |     |     |     | 60  |     |     |     |     |     |     | |
| gaa | ccg | gag | aca | gag | aaa | att | aat | gga | aaa | gat | tgc | ggc | ggt | gac | aag | 240 |
| Glu | Pro | Glu | Thr | Glu | Lys | Ile | Asn | Gly | Lys | Asp | Cys | Gly | Gly | Asp | Lys | |
| 65  |     |     |     |     | 70  |     |     |     |     | 75  |     |     |     |     | 80  | |
| gat | aag | att | gac | aat | cgc | gag | aat | cgt | ggg | agg | tcg | gat | att | aaa | ttc | 288 |
| Asp | Lys | Ile | Asp | Asn | Arg | Glu | Asn | Arg | Gly | Arg | Ser | Asp | Ile | Lys | Phe | |
|     |     |     |     | 85  |     |     |     |     | 90  |     |     |     |     | 95  |     | |
| acg | tac | cgg | cca | tcg | gtg | ccg | gct | cat | cga | gcg | ctc | agg | gag | agt | ccg | 336 |
| Thr | Tyr | Arg | Pro | Ser | Val | Pro | Ala | His | Arg | Ala | Leu | Arg | Glu | Ser | Pro | |
|     |     |     | 100 |     |     |     |     | 105 |     |     |     |     | 110 |     |     | |
| ctt | agc | tct | gat | gct | ata | ttt | aaa | caa | agt | cat | gca | ggt | ctg | ttc | aac | 384 |
| Leu | Ser | Ser | Asp | Ala | Ile | Phe | Lys | Gln | Ser | His | Ala | Gly | Leu | Phe | Asn | |
|     |     | 115 |     |     |     |     | 120 |     |     |     |     | 125 |     |     |     | |
| ctc | tgt | ata | gta | gtg | ctt | gtt | gct | gtt | aac | agc | agg | ctt | atc | att | gaa | 432 |
| Leu | Cys | Ile | Val | Val | Leu | Val | Ala | Val | Asn | Ser | Arg | Leu | Ile | Ile | Glu | |
|     | 130 |     |     |     |     | 135 |     |     |     |     | 140 |     |     |     |     | |
| aat | cta | atg | aag | tac | ggt | tgg | tta | att | aaa | acg | ggg | ttt | tgg | ttt | agt | 480 |
| Asn | Leu | Met | Lys | Tyr | Gly | Trp | Leu | Ile | Lys | Thr | Gly | Phe | Trp | Phe | Ser | |
| 145 |     |     |     |     | 150 |     |     |     |     | 155 |     |     |     |     | 160 | |
| tca | aga | tcg | ttg | aga | gat | tgg | ccc | ctt | ctt | atg | tgc | tgt | ctt | acc | ctc | 528 |
| Ser | Arg | Ser | Leu | Arg | Asp | Trp | Pro | Leu | Leu | Met | Cys | Cys | Leu | Thr | Leu | |
|     |     |     |     | 165 |     |     |     |     | 170 |     |     |     |     | 175 |     | |
| cct | ata | ttc | tct | ctt | gcc | gcc | tat | cta | gtt | gag | aag | ttg | gca | tat | cga | 576 |
| Pro | Ile | Phe | Ser | Leu | Ala | Ala | Tyr | Leu | Val | Glu | Lys | Leu | Ala | Tyr | Arg | |
|     |     |     | 180 |     |     |     |     | 185 |     |     |     |     | 190 |     |     | |
| aaa | tat | ata | tct | gca | cct | att | gtt | att | ttc | ttt | cat | atg | ctc | att | acc | 624 |
| Lys | Tyr | Ile | Ser | Ala | Pro | Ile | Val | Ile | Phe | Phe | His | Met | Leu | Ile | Thr | |
|     |     | 195 |     |     |     |     | 200 |     |     |     |     | 205 |     |     |     | |
| aca | aca | gca | gtt | ttg | tac | cca | gtt | tct | gtg | att | ctc | agt | tgt | ggg | tct | 672 |
| Thr | Thr | Ala | Val | Leu | Tyr | Pro | Val | Ser | Val | Ile | Leu | Ser | Cys | Gly | Ser | |
|     | 210 |     |     |     |     | 215 |     |     |     |     | 220 |     |     |     |     | |
| gct | gtt | ctg | tct | ggt | gtt | gca | ttg | atg | ctc | ttt | gct | tgt | atc | gtg | tgg | 720 |
| Ala | Val | Leu | Ser | Gly | Val | Ala | Leu | Met | Leu | Phe | Ala | Cys | Ile | Val | Trp | |
| 225 |     |     |     |     | 230 |     |     |     |     | 235 |     |     |     |     | 240 | |
| ttg | aaa | tta | gta | tct | tat | gca | cat | aca | aac | tat | gac | atg | aga | gcc | att | 768 |
| Leu | Lys | Leu | Val | Ser | Tyr | Ala | His | Thr | Asn | Tyr | Asp | Met | Arg | Ala | Ile | |
|     |     |     |     | 245 |     |     |     |     | 250 |     |     |     |     | 255 |     | |
| gcc | aac | tca | gct | gac | aag | gga | gat | gca | cta | tcc | gat | act | tca | ggt | gca | 816 |
| Ala | Asn | Ser | Ala | Asp | Lys | Gly | Asp | Ala | Leu | Ser | Asp | Thr | Ser | Gly | Ala | |
|     |     |     | 260 |     |     |     |     | 265 |     |     |     |     | 270 |     |     | |
| gat | tct | tca | cgt | gat | gtt | agc | ttc | aag | agt | ttg | gtc | tac | ttc | atg | gtt | 864 |
| Asp | Ser | Ser | Arg | Asp | Val | Ser | Phe | Lys | Ser | Leu | Val | Tyr | Phe | Met | Val | |
|     |     | 275 |     |     |     |     | 280 |     |     |     |     | 285 |     |     |     | |
| gct | cct | acg | cta | tgt | tac | cag | cca | agt | tat | cct | cga | aca | gat | tca | gtt | 912 |
| Ala | Pro | Thr | Leu | Cys | Tyr | Gln | Pro | Ser | Tyr | Pro | Arg | Thr | Asp | Ser | Val | |
|     | 290 |     |     |     |     | 295 |     |     |     |     | 300 |     |     |     |     | |
| aga | aag | ggt | tgg | gtg | gtt | cgt | caa | ttt | gtc | aag | tta | ata | ata | ttt | aca | 960 |
| Arg | Lys | Gly | Trp | Val | Val | Arg | Gln | Phe | Val | Lys | Leu | Ile | Ile | Phe | Thr | |
| 305 |     |     |     |     | 310 |     |     |     |     | 315 |     |     |     |     | 320 | |
| gga | ttc | atg | gga | ttt | atc | ata | gaa | caa | tat | atc | aat | cct | att | gtc | cag | 1008 |
| Gly | Phe | Met | Gly | Phe | Ile | Ile | Glu | Gln | Tyr | Ile | Asn | Pro | Ile | Val | Gln | |
|     |     |     |     | 325 |     |     |     |     | 330 |     |     |     |     | 335 |     | |
| aat | tca | caa | cat | ccc | tta | aag | ggg | gat | cta | tta | tat | gcc | att | gaa | agg | 1056 |
| Asn | Ser | Gln | His | Pro | Leu | Lys | Gly | Asp | Leu | Leu | Tyr | Ala | Ile | Glu | Arg | |
|     |     |     | 340 |     |     |     |     | 345 |     |     |     |     | 350 |     |     | |
| gtt | ttg | aag | ctc | tca | gtt | cca | aac | tta | tat | gtg | tgg | ctt | tgc | atg | ttc | 1104 |
| Val | Leu | Lys | Leu | Ser | Val | Pro | Asn | Leu | Tyr | Val | Trp | Leu | Cys | Met | Phe | |
|     |     | 355 |     |     |     |     | 360 |     |     |     |     | 365 |     |     |     | |

-continued

```
tac tgc ttt ttt cat cta tgg tta aat ata ctt gct gag ctc ctt cgg      1152
Tyr Cys Phe Phe His Leu Trp Leu Asn Ile Leu Ala Glu Leu Leu Arg
    370                 375                 380 ttt ggt gac aga gag ttc tat aaa gat tgg tgg aat gca agg acc gtt      1200
Phe Gly Asp Arg Glu Phe Tyr Lys Asp Trp Trp Asn Ala Arg Thr Val
385                 390                 395                 400 gag gag tac tgg aga atg tgg aat atg cct gtt cat aag tgg atg gtt      1248
Glu Glu Tyr Trp Arg Met Trp Asn Met Pro Val His Lys Trp Met Val
                405                 410                 415 cgc cat atc tac ttt cca tgc ttg cgg cat aaa ata cca agg ggg gta      1296
Arg His Ile Tyr Phe Pro Cys Leu Arg His Lys Ile Pro Arg Gly Val
            420                 425                 430 gcc ttg tta att gct ttc ttc gtt tca gct gta ttt cat gag ttg tgc      1344
Ala Leu Leu Ile Ala Phe Phe Val Ser Ala Val Phe His Glu Leu Cys
        435                 440                 445 att gct gtt cct tgc cac atg ttc aag ctc tgg gct ttt att gga att      1392
Ile Ala Val Pro Cys His Met Phe Lys Leu Trp Ala Phe Ile Gly Ile
    450                 455                 460 atg ttt cag att cca ttg gtc ggg atc act aat tac ctc cag aac aag      1440
Met Phe Gln Ile Pro Leu Val Gly Ile Thr Asn Tyr Leu Gln Asn Lys
465                 470                 475                 480 ttc aga agc tcc atg gtg gga aat atg atc ttt tgg ttc att ttc tgc      1488
Phe Arg Ser Ser Met Val Gly Asn Met Ile Phe Trp Phe Ile Phe Cys
                485                 490                 495 att ctt ggt caa ccc atg tgt gtg cta ttg tat tat cat gac cta atg      1536
Ile Leu Gly Gln Pro Met Cys Val Leu Leu Tyr Tyr His Asp Leu Met
            500                 505                 510 aat cgg aaa ggc aat gct gaa tta aga tga                              1566
Asn Arg Lys Gly Asn Ala Glu Leu Arg
        515                 520
```

<210> SEQ ID NO 14
<211> LENGTH: 521
<212> TYPE: PRT
<213> ORGANISM: Jatropha curcas

<400> SEQUENCE: 14

```
Met Thr Ile Leu Glu Thr Thr Thr Ser Gly Gly Asp Gly Val Ala Glu
1               5                   10                  15

Ser Ser Ser Asp Leu Asn Val Ser Leu Arg Arg Arg Lys Gly Thr
            20                  25                  30

Ser Ser Asp Gly Ala Leu Pro Glu Leu Thr Ser Asn Ile Val Glu Leu
        35                  40                  45

Glu Ser Glu Ser Gly Gly Gln Val Met Met Asp Pro Val Val Thr
    50                  55                  60

Glu Pro Glu Thr Glu Lys Ile Asn Gly Lys Asp Cys Gly Gly Lys Asp
65                  70                  75                  80

Asp Lys Ile Asp Asn Arg Glu Asn Arg Gly Arg Ser Asp Ile Lys Phe
                85                  90                  95

Thr Tyr Arg Pro Ser Val Pro Ala His Arg Ala Leu Arg Glu Ser Pro
            100                 105                 110

Leu Ser Ser Asp Ala Ile Phe Lys Gln Ser His Ala Gly Leu Phe Asn
        115                 120                 125

Leu Cys Ile Val Val Leu Val Ala Val Asn Ser Arg Leu Ile Ile Glu
    130                 135                 140

Asn Leu Met Lys Tyr Gly Trp Leu Ile Lys Thr Gly Phe Trp Phe Ser
145                 150                 155                 160

Ser Arg Ser Leu Arg Asp Trp Pro Leu Leu Met Cys Cys Leu Thr Leu
                165                 170                 175
```

```
Pro Ile Phe Ser Leu Ala Ala Tyr Leu Val Glu Lys Leu Ala Tyr Arg
            180                 185                 190

Lys Tyr Ile Ser Ala Pro Ile Val Phe Phe His Met Leu Ile Thr
    195                 200                 205

Thr Thr Ala Val Leu Tyr Pro Val Ser Val Ile Leu Ser Cys Gly Ser
210                 215                 220

Ala Val Leu Ser Gly Val Ala Leu Met Leu Phe Ala Cys Ile Val Trp
225                 230                 235                 240

Leu Lys Leu Val Ser Tyr Ala His Thr Asn Tyr Asp Met Arg Ala Ile
            245                 250                 255

Ala Asn Ser Ala Asp Lys Gly Asp Ala Leu Ser Asp Thr Ser Gly Ala
            260                 265                 270

Asp Ser Ser Arg Asp Val Ser Phe Lys Ser Leu Val Tyr Phe Met Val
            275                 280                 285

Ala Pro Thr Leu Cys Tyr Gln Pro Ser Tyr Pro Arg Thr Asp Ser Val
            290                 295                 300

Arg Lys Gly Trp Val Val Arg Gln Phe Val Lys Leu Ile Ile Phe Thr
305                 310                 315                 320

Gly Phe Met Gly Phe Ile Ile Glu Gln Tyr Ile Asn Pro Ile Val Gln
            325                 330                 335

Asn Ser Gln His Pro Leu Lys Gly Asp Leu Leu Tyr Ala Ile Glu Arg
            340                 345                 350

Val Leu Lys Leu Ser Val Pro Asn Leu Tyr Val Trp Leu Cys Met Phe
            355                 360                 365

Tyr Cys Phe Phe His Leu Trp Leu Asn Ile Leu Ala Glu Leu Leu Arg
            370                 375                 380

Phe Gly Asp Arg Glu Phe Tyr Lys Asp Trp Trp Asn Ala Arg Thr Val
385                 390                 395                 400

Glu Glu Tyr Trp Arg Met Trp Asn Met Pro Val His Lys Trp Met Val
            405                 410                 415

Arg His Ile Tyr Phe Pro Cys Leu Arg His Lys Ile Pro Arg Gly Val
            420                 425                 430

Ala Leu Leu Ile Ala Phe Phe Val Ser Ala Val Phe His Glu Leu Cys
            435                 440                 445

Ile Ala Val Pro Cys His Met Phe Lys Leu Trp Ala Phe Ile Gly Ile
            450                 455                 460

Met Phe Gln Ile Pro Leu Val Gly Ile Thr Asn Tyr Leu Gln Asn Lys
465                 470                 475                 480

Phe Arg Ser Ser Met Val Gly Asn Met Ile Phe Trp Phe Ile Phe Cys
            485                 490                 495

Ile Leu Gly Gln Pro Met Cys Val Leu Leu Tyr Tyr His Asp Leu Met
            500                 505                 510

Asn Arg Lys Gly Asn Ala Glu Leu Arg
            515                 520

<210> SEQ ID NO 15
<211> LENGTH: 1164
<212> TYPE: DNA
<213> ORGANISM: Ricinus communis
<220> FEATURE:
<221> NAME/KEY: CDS
<222> LOCATION: (1)..(1164)

<400> SEQUENCE: 15 atg gga ggt ggt ggt cgc atg tct act gtc ata acc agc aac aac agt      48
Met Gly Gly Gly Gly Arg Met Ser Thr Val Ile Thr Ser Asn Asn Ser
```

-continued

| 1 | | | | 5 | | | | 10 | | | | 15 | | | | |
|---|---|---|---|---|---|---|---|---|---|---|---|---|---|---|---|---|
| gag | aag | aaa | gga | gga | agc | agc | cac | ctt | aag | cga | gcg | ccg | cac | acg | aag | 96 |
| Glu | Lys | Lys | Gly | Gly | Ser | Ser | His | Leu | Lys | Arg | Ala | Pro | His | Thr | Lys | |
| | | | 20 | | | | | 25 | | | | | 30 | | | |
| cct | cct | ttc | aca | ctt | ggt | gac | ctc | aag | aga | gcc | atc | cca | ccc | cat | tgc | 144 |
| Pro | Pro | Phe | Thr | Leu | Gly | Asp | Leu | Lys | Arg | Ala | Ile | Pro | Pro | His | Cys | |
| | | | 35 | | | | | 40 | | | | | 45 | | | |
| ttt | gaa | cgc | tct | ttt | gtg | cgc | tca | ttc | tcc | tat | gtt | gcc | tat | gat | gtc | 192 |
| Phe | Glu | Arg | Ser | Phe | Val | Arg | Ser | Phe | Ser | Tyr | Val | Ala | Tyr | Asp | Val | |
| | | | 50 | | | | | 55 | | | | | 60 | | | |
| tgc | tta | agt | ttt | ctt | ttc | tac | tcg | atc | gcc | acc | aac | ttc | ttc | cct | tac | 240 |
| Cys | Leu | Ser | Phe | Leu | Phe | Tyr | Ser | Ile | Ala | Thr | Asn | Phe | Phe | Pro | Tyr | |
| 65 | | | | | 70 | | | | | 75 | | | | | 80 | |
| atc | tct | tct | ccg | ctc | tcg | tat | gtc | gct | tgg | ctg | gtt | tac | tgg | ctc | ttc | 288 |
| Ile | Ser | Ser | Pro | Leu | Ser | Tyr | Val | Ala | Trp | Leu | Val | Tyr | Trp | Leu | Phe | |
| | | | | 85 | | | | | 90 | | | | | 95 | | |
| caa | ggc | tgc | att | ctc | act | ggt | ctt | tgg | gtc | atc | ggc | cat | gaa | tgt | ggc | 336 |
| Gln | Gly | Cys | Ile | Leu | Thr | Gly | Leu | Trp | Val | Ile | Gly | His | Glu | Cys | Gly | |
| | | | 100 | | | | | 105 | | | | | 110 | | | |
| cat | cat | gct | ttt | agt | gag | tat | cag | ctg | gct | gat | gac | att | gtt | ggc | cta | 384 |
| His | His | Ala | Phe | Ser | Glu | Tyr | Gln | Leu | Ala | Asp | Asp | Ile | Val | Gly | Leu | |
| | | | 115 | | | | | 120 | | | | | 125 | | | |
| att | gtc | cat | tct | gca | ctt | ctg | gtt | cca | tat | ttt | tca | tgg | aaa | tat | agc | 432 |
| Ile | Val | His | Ser | Ala | Leu | Leu | Val | Pro | Tyr | Phe | Ser | Trp | Lys | Tyr | Ser | |
| | | | 130 | | | | | 135 | | | | | 140 | | | |
| cat | cgc | cgc | cac | cat | tct | aac | ata | gga | tct | ctc | gag | cga | gac | gaa | gtg | 480 |
| His | Arg | Arg | His | His | Ser | Asn | Ile | Gly | Ser | Leu | Glu | Arg | Asp | Glu | Val | |
| 145 | | | | | 150 | | | | | 155 | | | | | 160 | |
| ttc | gtc | ccg | aaa | tca | aag | tcg | aaa | att | tca | tgg | tat | tct | aag | tac | tca | 528 |
| Phe | Val | Pro | Lys | Ser | Lys | Ser | Lys | Ile | Ser | Trp | Tyr | Ser | Lys | Tyr | Ser | |
| | | | | 165 | | | | | 170 | | | | | 175 | | |
| aac | aac | ccg | cca | ggt | cga | gtt | ttg | aca | ctt | gct | gcc | acg | ctc | ctc | ctt | 576 |
| Asn | Asn | Pro | Pro | Gly | Arg | Val | Leu | Thr | Leu | Ala | Ala | Thr | Leu | Leu | Leu | |
| | | | 180 | | | | | 185 | | | | | 190 | | | |
| ggc | tgg | cct | tta | tac | tta | gct | ttc | aat | gtc | tct | ggt | aga | cct | tac | gat | 624 |
| Gly | Trp | Pro | Leu | Tyr | Leu | Ala | Phe | Asn | Val | Ser | Gly | Arg | Pro | Tyr | Asp | |
| | | | 195 | | | | | 200 | | | | | 205 | | | |
| cgc | ttt | gct | tgc | cat | tat | gat | ccc | tat | ggc | cca | ata | ttt | tcc | gaa | aga | 672 |
| Arg | Phe | Ala | Cys | His | Tyr | Asp | Pro | Tyr | Gly | Pro | Ile | Phe | Ser | Glu | Arg | |
| | 210 | | | | | 215 | | | | | 220 | | | | | |
| gaa | agg | ctt | cag | att | tac | att | gct | gac | ctc | gga | atc | ttt | gcc | aca | acg | 720 |
| Glu | Arg | Leu | Gln | Ile | Tyr | Ile | Ala | Asp | Leu | Gly | Ile | Phe | Ala | Thr | Thr | |
| 225 | | | | | 230 | | | | | 235 | | | | | 240 | |
| ttt | gtg | ctt | tat | cag | gct | aca | atg | gca | aaa | ggg | ttg | gct | tgg | gta | atg | 768 |
| Phe | Val | Leu | Tyr | Gln | Ala | Thr | Met | Ala | Lys | Gly | Leu | Ala | Trp | Val | Met | |
| | | | | 245 | | | | | 250 | | | | | 255 | | |
| cgt | atc | tat | ggg | gtg | cca | ttg | ctt | att | gtt | aac | tgt | ttc | ctt | gtt | atg | 816 |
| Arg | Ile | Tyr | Gly | Val | Pro | Leu | Leu | Ile | Val | Asn | Cys | Phe | Leu | Val | Met | |
| | | | 260 | | | | | 265 | | | | | 270 | | | |
| atc | aca | tac | ttg | cag | cac | act | cac | cca | gct | att | cca | cgc | tat | ggc | tca | 864 |
| Ile | Thr | Tyr | Leu | Gln | His | Thr | His | Pro | Ala | Ile | Pro | Arg | Tyr | Gly | Ser | |
| | | | 275 | | | | | 280 | | | | | 285 | | | |
| tcg | gaa | tgg | gat | tgg | ctc | cgg | gga | gca | atg | gtg | act | gtc | gat | aga | gat | 912 |
| Ser | Glu | Trp | Asp | Trp | Leu | Arg | Gly | Ala | Met | Val | Thr | Val | Asp | Arg | Asp | |
| | | | 290 | | | | | 295 | | | | | 300 | | | |
| tat | ggg | gtg | ttg | aat | aaa | gta | ttc | cat | aac | att | gca | gac | act | cat | gta | 960 |
| Tyr | Gly | Val | Leu | Asn | Lys | Val | Phe | His | Asn | Ile | Ala | Asp | Thr | His | Val | |
| 305 | | | | | 310 | | | | | 315 | | | | | 320 | |
| gct | cat | cat | ctc | ttt | gct | aca | gtg | cca | cat | tac | cat | gca | atg | gag | gcc | 1008 |
| Ala | His | His | Leu | Phe | Ala | Thr | Val | Pro | His | Tyr | His | Ala | Met | Glu | Ala | |

```
                    325                 330                 335
act aaa gca atc aag cct ata atg ggt gag tat tac cgg tat gat ggt    1056
Thr Lys Ala Ile Lys Pro Ile Met Gly Glu Tyr Tyr Arg Tyr Asp Gly
            340                 345                 350 acc cca ttt tac aag gca ttg tgg agg gag gca aag gag tgc ttg ttc    1104
Thr Pro Phe Tyr Lys Ala Leu Trp Arg Glu Ala Lys Glu Cys Leu Phe
        355                 360                 365 gtc gag cca gat gaa gga gct cct aca caa ggc gtt ttc tgg tac cgg    1152
Val Glu Pro Asp Glu Gly Ala Pro Thr Gln Gly Val Phe Trp Tyr Arg
    370                 375                 380 aac aag tat taa                                                    1164
Asn Lys Tyr
385

<210> SEQ ID NO 16
<211> LENGTH: 387
<212> TYPE: PRT
<213> ORGANISM: Ricinus communis

<400

-continued

```
Ser Glu Trp Asp Trp Leu Arg Gly Ala Met Val Thr Val Asp Arg Asp
    290                 295             300

Tyr Gly Val Leu Asn Lys Val Phe His Asn Ile Ala Asp Thr His Val
305                 310             315                 320

Ala His His Leu Phe Ala Thr Val Pro His Tyr His Ala Met Glu Ala
            325                 330             335

Thr Lys Ala Ile Lys Pro Ile Met Gly Glu Tyr Tyr Arg Tyr Asp Gly
            340             345                 350

Thr Pro Phe Tyr Lys Ala Leu Trp Arg Glu Ala Lys Glu Cys Leu Phe
        355                 360             365

Val Glu Pro Asp Glu Gly Ala Pro Thr Gln Gly Val Phe Trp Tyr Arg
    370                 375             380

Asn Lys Tyr
385
```